United States Patent
Daniels et al.

(10) Patent No.: US 10,138,208 B2
(45) Date of Patent: Nov. 27, 2018

(54) PYRAZOLE DERIVATIVES AS INHIBITORS OF STAT3

(71) Applicant: Mayo Foundation for Medical Education and Research, Rochester, MN (US)

(72) Inventors: David J. Daniels, Rochester, MN (US); Ian F. Parney, Rochester, MN (US); Timothy E. Peterson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/643,373

(22) Filed: Jul. 6, 2017

(65) Prior Publication Data

US 2018/0002290 A1    Jan. 4, 2018

Related U.S. Application Data

(63) Continuation of application No. 14/407,781, filed as application No. PCT/US2013/031227 on Mar. 14, 2013, now Pat. No. 9,732,038.

(60) Provisional application No. 61/659,924, filed on Jun. 14, 2012.

(51) Int. Cl.
| | | |
|---|---|---|
| C07D 231/12 | (2006.01) |
| A61K 45/06 | (2006.01) |
| A61K 31/495 | (2006.01) |
| A61K 31/415 | (2006.01) |
| A61K 31/4155 | (2006.01) |
| A61K 39/00 | (2006.01) |
| G01N 33/53 | (2006.01) |
| C07D 231/00 | (2006.01) |
| C07D 231/02 | (2006.01) |
| C07D 231/10 | (2006.01) |

(52) U.S. Cl.
CPC .......... *C07D 231/12* (2013.01); *A61K 31/415* (2013.01); *A61K 31/4155* (2013.01); *A61K 31/495* (2013.01); *A61K 39/0011* (2013.01); *A61K 45/06* (2013.01); *C07D 231/00* (2013.01); *C07D 231/02* (2013.01); *C07D 231/10* (2013.01); *G01N 33/5308* (2013.01)

(58) Field of Classification Search
CPC .............. A61K 31/415; A61K 31/4155; A61K 31/495; A61K 45/06; A61K 39/0011; C07D 231/12; C07D 231/10; C07D 231/02; C07D 231/00
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,710,795 A | 1/1973 | Higuchi et al. |
| 3,836,522 A | 9/1974 | Somlo et al. |
| 3,845,770 A | 11/1974 | Theeuwes et al. |
| 3,916,899 A | 11/1975 | Theeuwes et al. |
| RE28,819 E | 5/1976 | Thompson |
| 4,008,719 A | 2/1977 | Theeuwes et al. |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 4,710,384 A | 12/1987 | Rotman |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,092,877 A | 3/1992 | Pinchuk |
| 5,120,548 A | 6/1992 | McClelland et al. |
| 5,323,907 A | 6/1994 | Kalvelage |
| 5,354,556 A | 10/1994 | Sparks et al. |
| 5,466,823 A | 11/1995 | Talley et al. |
| 5,591,767 A | 1/1997 | Mohr et al. |
| 5,639,476 A | 6/1997 | Oshlack et al. |
| 5,674,533 A | 10/1997 | Santus et al. |
| 5,709,874 A | 1/1998 | Hanson et al. |
| 5,733,566 A | 3/1998 | Lewis |
| 5,759,542 A | 6/1998 | Gurewich |
| 5,760,068 A | 6/1998 | Talley et al. |
| 5,840,674 A | 11/1998 | Yatvin et al. |

(Continued)

FOREIGN PATENT DOCUMENTS

| | | |
|---|---|---|
| EP | 0248594 | 12/1987 |
| FR | 2135001 | 8/1972 |
| JP | 2006-316054 | 11/2006 |
| WO | WO 1995/015316 | 6/1995 |
| WO | WO 2008/017932 | 2/2008 |
| WO | WO 2009/149192 | 12/2009 |

OTHER PUBLICATIONS

Agarwal et al., "Cox-2 is needed but not sufficient for apoptosis induced by Cox-2 selective inhibitors in colon cancer cells," *Apoptosis.*, 8(6):649-654, Dec. 2003.

(Continued)

*Primary Examiner* — Jeffrey S Lundgren
*Assistant Examiner* — Stephanie K Springer
(74) *Attorney, Agent, or Firm* — Fish & Richardson P.C.

(57) ABSTRACT

Compositions that modulate the activity of signal transducer and activator of transcription-3 (STAT3) activity as well as their methods of use, such as treatment and imaging are provided. Compositions contain small molecules such as substituted pyrazoles and are useful in treatment of diseases related to the activity of STAT3 including, for example, cancer and other diseases.

9 Claims, 13 Drawing Sheets

(56) References Cited

U.S. PATENT DOCUMENTS

| | | | |
|---|---|---|---|
| 5,860,957 A | 1/1999 | Jacobsen et al. | |
| 5,900,252 A | 5/1999 | Calanchi et al. | |
| 5,948,433 A | 9/1999 | Burton et al. | |
| 5,972,366 A | 10/1999 | Haynes et al. | |
| 5,983,134 A | 11/1999 | Ostrow | |
| 5,985,307 A | 11/1999 | Hanson et al. | |
| 5,985,317 A | 11/1999 | Venkateshwaran et al. | |
| 6,004,534 A | 12/1999 | Langer et al. | |
| 6,010,715 A | 1/2000 | Wick et al. | |
| 6,024,975 A | 2/2000 | D'Angelo et al. | |
| 6,039,975 A | 3/2000 | Shah et al. | |
| 6,048,736 A | 4/2000 | Kosak | |
| 6,060,082 A | 5/2000 | Chen et al. | |
| 6,071,495 A | 6/2000 | Unger et al. | |
| 6,120,751 A | 9/2000 | Unger | |
| 6,131,570 A | 10/2000 | Schuster et al. | |
| 6,139,865 A | 10/2000 | Friend et al. | |
| 6,156,781 A * | 12/2000 | Talley ................. | C07D 231/12 514/236.5 |
| 6,167,301 A | 12/2000 | Flower et al. | |
| 6,253,872 B1 | 7/2001 | Neumann | |
| 6,256,533 B1 | 7/2001 | Yuzhakov et al. | |
| 6,261,595 B1 | 7/2001 | Stanley et al. | |
| 6,267,983 B1 | 7/2001 | Fujii et al. | |
| 6,271,359 B1 | 8/2001 | Norris et al. | |
| 6,274,552 B1 | 8/2001 | Tamarkin et al. | |
| 6,316,652 B1 | 11/2001 | Steliou | |

OTHER PUBLICATIONS

Ansel, "Pemral Solids, Capsules, Tablets, and Controlled-Release Dosage Forms," *Introduction to Pharmaceutical Dosage Forms*, 4th Edition, pp. 126-141, 1985.

Ball et al., "The small molecule, LLL12, inhibits STAT3 phosphorylation and induces apoptosis in medulloblastoma and glioblastoma cells," *PLoS One*, 6(4):e18820, 10 pages, Apr. 19, 2011.

Ball, "Small molecule inhibitors, LLL12 and celecoxib, effectively inhibit STAT3 phosphorylation, decrease cellular viability and induce apoptosis in medulloblastoma and glioblastoma cell lines," [dissertation] The Ohio State University, 114 pages, 2011.

Barbey et al., "Synthesis and activity of a new methoxytetrahydropyran derivative as dual cyclooxygenase-2/5-lipoxygenase inhibitor," *Bioorg Med Chem Lett.*, 12(5):779-782, Mar. 11, 2002.

Becker et al., "Three-dimensional structure of the Stat3beta homodimer bound to DNA," *Nature*, 394(6689):145-151, Jul. 9, 1998.

Boockvar et al., "Safety and maximum tolerated dose of superselective intraarterial cerebral infusion of bevacizumab after osmotic blood-brain barrier disruption for recurrent malignant gliomas. Clinical article," *J Neurosurg.*, 114(3):624-632, Epub Oct. 22, 2010.

Brantley and Benveniste, "Signal transducer and activator of transcription-3: a molecular hub for signaling pathways in gliomas," *Mol Cancer Res.*, 6(5):675-684, May 2008.

Brantley et al., "Signal transducer and activator of transcription-3: a molecular hub for signaling pathways in gliomas," *Mol Cancer Res.*, 6(5):675-684, May 2008.

Braunstein et al., "STATs dimerize in the absence of phosphorylation," *J Biol Chem.*, 278(36):34133-34140, Epub Jun. 28, 2003.

Bromberg, "Stat proteins and oncogenesis," *J Clin Invest.*, 109(9):1139-1142, May 2002.

Brown et al., "The role of apoptosis in cancer development and treatment response," *Nat Rev Cancer.*, 5(3):231-237, Mar. 2005.

Daniel et al., "Inhibition of STAT3 signaling prevents vascular smooth muscle cell proliferation and neointima formation," *Basic Res Cardiol.*, 107(3):261, Epub Mar. 15, 2012.

Daniels et al., "A bivalent ligand (KDAN-18) containing delta-antagonist and kappa-agonist pharmacophores bridges delta2 and kappa1 opioid receptor phenotypes," *J Med Chem.*, 48(6):1713-1716, Mar. 24, 2005.

Daniels et al., "Opioid-induced tolerance and dependence in mice is modulated by the distance between pharmacophores in a bivalent ligand series," *Proc Natl Acad Sci U S A.*, 102(52):19208-19213, Epub Dec. 19, 2005.

Daniels et al., "Rational structure-based design and evaluation of novel STAT3 inhibitors targeting malignant brain tumors," c. 2012 Mayo Foundation for Medical Education and Research [poster], 1 page.

Darnell, "STATs and Gene Regulation," *Science*, 277(5332):1630-1635, Sep. 12, 1997.

Dey et al., "The role of glioma microenvironment in immune modulation: potential targets for intervention," *Lett Drug Des Discov.*, 3(7):443-451, Sep. 2006.

European Search Report for Application No. 13804641.2, dated Nov. 13, 2015.

Fletcher et al., "Antagonism of the Stat3-Stat3 protein dimer with salicylic acid based small molecules," *ChemMedChem.* 6(8):1459-1470, Epub May 25, 2011.

Fossati et al., "Pediatric medulloblastoma: toxicity of current treatment and potential role of protontherapy," *Cancer Treat Rev.*, 35(1):79-96, Epub Oct. 30, 2008.

Friesner et al., "Glide: A New Approach for Rapid, Accurate Docking and Scoring. 1. Method and Assessment of Docking Accuracy," *J Med Chem.*, 47:1739-1749, 2004.

Gomez et al., "Design, synthesis, and evaluation of peptidomimetics containing Freidinger lactams as STAT3 inhibitors," *Bioorg Med Chem Lett.*, 19(6):1733-1736, Epub Jan. 31, 2009.

Gunning et al., "Targeting protein-protein interactions: suppression of Stat3 dimerization with rationally designed small-molecule, nonpeptidic S142 domain binders," *Chembiochem.*, 9(17):2800-2803, Nov. 24, 2008.

Heinrich et al., "Interleukin-6-type cytokine signalling through the gp130/Jak/STAT pathway," *Biochem J.*, 334 (Pt 2):297-314, Sep. 1, 1998.

Hussain et al., "A novel small molecule inhibitor of signal transducers and activators of transcription 3 reverses immune tolerance in malignant glioma patients," *Cancer Res.*, 67(20):9630-9636, Oct. 15, 2007.

Hwang et al., "Synthesis and structure-activity relationship studies of urea-containing pymzoles as dual inhibitors of cyclooxygenase-2 and soluble epoxide hydrolase," *J Med Chem.*,54(8):3037-3050, Epub Apr. 5, 2011.

International Preliminary Report on Patentability for PCT/US2013/031227 dated Dec. 24, 2014, 9 pages.

International Search Report and Written Opinion for PCT/US2013/031227 dated Aug. 15, 2013, 12 pages.

IUPAC-IUB Commission on Biochemical Nomenclature, Abbreviated Nomenclature of Synthetic Polypeptides (Polymerized Amino Acids), Revised Recommindations (1971) *Biochem*. 11(5):942-944, 1972.

Iwamaru et al., "A novel inhibitor of the STAT3 pathway induces apoptosis in malignant glioma cells both in vitro and in vivo," *Oncogene*, 26(17):2435-2444, Epub Oct. 16, 2006.

Kitange et al., "Evaluation of MGMT promoter methylation status and correlation with temozolomide response in orthotopic glioblastoma xenograft model," *J Neurooncol.*, 92(1):23-31, Epub Nov. 15, 2008.

Kohsaka et al., "STAT3 inhibition overcomes temozolomide resistance in glioblastoma by downregulating MGMT expression," *Mol Cancer Ther.*, 11(6):1289-1299, Epub Apr. 24, 2012.

Konnikova et al., "Knockdown of STAT3 expression by RNAi induces apoptosis in astmcytoma cells," *BMC Cancer.*, 3:23, Sep. 17, 2003.

Li et al., "Fragment-based drug design and drug repositioning using multiple ligand simultaneous docking (MLSD): identifying celecoxib and template compounds as novel inhibitors of signal transducer and activator of transcription 3 (STAT3)," *J Med Chem.*, 54(15):5592-5596, Epub Jul. 8, 2011.

Lin et al., "A novel small molecule, LLL12, inhibits STAT3 phosphorylation and activities and exhibits potent growth-suppressive activity in human cancer cells," *Neoplasia.*, 12(1):39-50, Jan. 2010.

Liu et al., "Novel small molecule, XZH-5, inhibits constitutive and interleukin-6-induced STAT3 phosphorylation in human rhabdomyosarcoma cells," *Cancer Sci.*, 102(7):1381-1387, Epub May 5, 2011.

Meydan et al., "Inhibition of acute lymphoblastic leukaemia by a Jak-2 inhibitor," *Nature*, 379(6566):645-648, Feb. 15, 1996.

(56) References Cited

OTHER PUBLICATIONS

Murphy et al., "Silencing of the miR-17~92 cluster family inhibits medulloblastoma progression," *Cancer Res.*, 73(23):7068-7078, Epub Oct. 21, 2013.
NCT00955812 "STAT3 Inhibitor for Solid Tumors," Clinical Trials. gov, 3 pages, Feb. 2013.
Neidle, "Failure modes in the discovery process," *Cancer Drug Design and Discovery*, 427-431, 2008.
O'Farrell et al., "IL-10 inhibits macrophage activation and proliferation by distinct signaling mechanisms: evidence for Stat3-dependent and-independent pathways," *EMBO J.*, 17(4):1006-1018, Feb. 16, 1998.
Page et al., "Identification of a non-phosphorylated, cell permeable, small molecule ligand for the Stat3 SH2 domain," *Bioorg Med Chem Lett.*, 21(18):5605-5609, Epub Jun. 30, 2011.
Pajouhesh and Lenz, "Medicinal chemical properties of successful central nervous system drugs," *NeuroRx.*, 2(4):541-553, Oct 2005.
Penning et al., "Synthesis and biological evaluation of the 1,5-diarylpyrazole class of cyclooxygenase-2 inhibitors: identification of 4-[5-(4-methylphenyl)-3-(trifluoromethyl)-1H-pyrazol-1-yl]benze nesulfonamide (SC-58635, celecoxib)," *J Med Chem.*, 40(9):1347-1365, Apr. 25, 1997.
Rahaman et al., "Inhibition of constitutively active Stat3 suppresses proliferation and induces apoptosis in glioblastoma multiforme cells," *Oncogene.*, 21(55):8404-8413, Dec. 5, 2002.
Reed et al., "Celecoxib inhibits STAT3 phosphorylation and suppresses cell migration and colony forming ability in rhabdomyosarcoma cells," *Biochem Biophys Res Commun.*, 407(3):450-455, Epub Mar. 21, 2011.
Ren et al., "Identification of a high-affinity phosphopeptide inhibitor of Stat3," *Bioorg Med Chem Lett.*, 13(4):633-636, Feb. 24, 2003.
Schaefer et al., "Constitutive activation of Stat3alpha in brain tumors localization to tumor endothelial cells and activation by the endothelial tyrosine kinase receptor (VEGFR-2)," *Oncogene* 21(13):2058-2065, Mar. 27, 2002.
Schust and Berg, "A high-throughput fluorescence polarization assay for signal transducer and activator of transcription 3," *Anal. Biochem.*, 330(1):114-118, Jul. 1, 2004.
Schust et al., "Stattic: a small-molecule inhibitor of STAT3 activation and dimerization," *Chem Biol.*, 13(11):1235-1242, Nov. 2006.
Senft et al., "Inhibition of the JAK-2/STAT3 signaling pathway impedes the migratory and invasive potential of human glioblastoma cells," *J Neurooncol.*, 101(3):393-403, Epub Jun. 30, 2010.
Siddiquee et al., "An oxazole-based small-molecule Stat3 inhibitor modulates Stat3 stability and processing and induces antitumor cell effects," *ACS Chem Biol.*, 2(12):787-798, Dec. 21, 2007.
Siddiquee et al., "Selective chemical probe inhibitor of Stat3, identified through structure-based virtual screening, induces antitumor activity," *Proc Nati Acad Sci U S A.*, 104(18):7391-7396. Epub Apr. 26, 2007.
Singh et al., "Modified reaction conditions to achieve high regioselectivity in the two component synthesis of 1,5-diarylpyrazoles," *Tetrahedron Letters*, 45(41):7679-7682, Oct. 4, 2004.
Siu et al., "Coexpression of neuronatin splice forms promotes medulloblastoma growth," *Neuro Oncol.*, 10(5):716-724, Epub Aug. 13, 2008.
Song et al., "A low-molecular-weight compound discovered through virtual database screening inhibits Stat3 function in breast cancer cells," *Proc Natl Acad Sci U S A.*, 102(13):4700-4705, Epub Mar. 21, 2005.
Stupp et al., "Radiotherapy plus concomitant and adjuvant temozolomide for glioblastoma," *N Engl J Med.*, 352(10):987-996, Mar. 10, 2005.
Turkson et al., "Phosphotyrosyl peptides block Stat3-mediated DNA binding activity, gene regulation, and cell transformation," *J Biol Chem.*, 276(48):45443-45455, Epub Sep. 28, 2001.
Uddin et al., "[I]-Celecoxib Analogues as SPECT Tracers of Cyclooxygenase-2 in Inflammation," *ACS Med Chem Lett.*, 2(2):160-164, Feb. 10, 2011.
Valera et al., "Pediatric glioblastoma cell line shows different patterns of expression of transmembrane ABC transporters after in vitro exposure to vinblastine," Childs Nerv Syst., 25(1):39-45, Epub Oct. 23, 2008, print Jan. 2009.
Wybranska et al., "Apoptosis-related gene expression in glioblastoma (LN-18) and medulloblastoma (Daoy) cell lines," Hum Cell., 26(4):137-148, Epub Sep. 15, 2013.
Yang et al., "Sorafenib inhibits signal transducer and activator of transcription 3 signaling associated with growth arrest and apoptosis of medulloblastomas," *Mol Cancer Ther.*, 7(11):3519-3526, Nov. 2008.
Yu and Jove, "The STATs of cancer—new molecular targets come of age," *Nat Rev Cancer.*, 4(2):97-105, Feb. 2004.
Yu et al., "Crosstalk between cancer and immune cells: role of STAT3 in the tumour microenvironment," *Nat Rev Immunol.*, 7(1):41-51, Jan. 2007.
Yu et al., "Enhanced DNA-binding activity of a Stat3-related protein in cells transformed by the Src oncoprotein," *Science*, 269(5220):81-83, Jul. 7, 1995.
Yu et al., "STATs in cancer inflammation and immunity: a leading role for STAT3," *Nat Rev Cancer.*, 9(11):798-809, Nov. 2009.
Yue and Turkson, "Targeting STAT3 in cancer: how successful are we?" *Expert Opin Investig Drugs*, 18(1):45-56, Jan. 2009.
Zhang et al, "A novel small-molecule disrupts Stat3 SH2 domain-phosphotyrosine interactions and Stat3-dependent tumor processes," *Biochem Pharmacol.*, 79(10):1398-1409, May 15, 2010.
European Communication Pursuant to Article 94(3) EPC in International Application No. 13804641.2, dated Mar. 21, 2017, 5 pages.

\* cited by examiner

FIG. 11  Plasma Stability
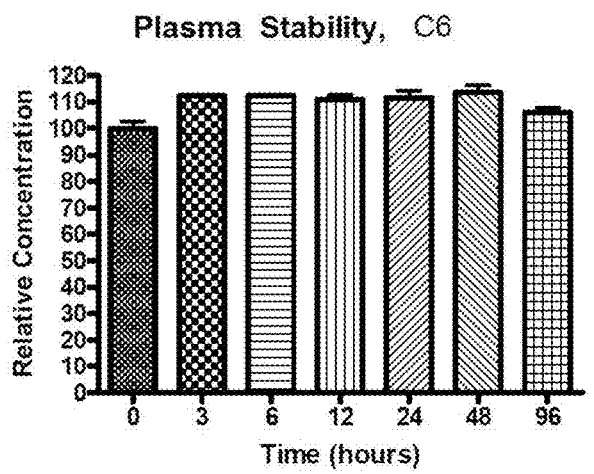
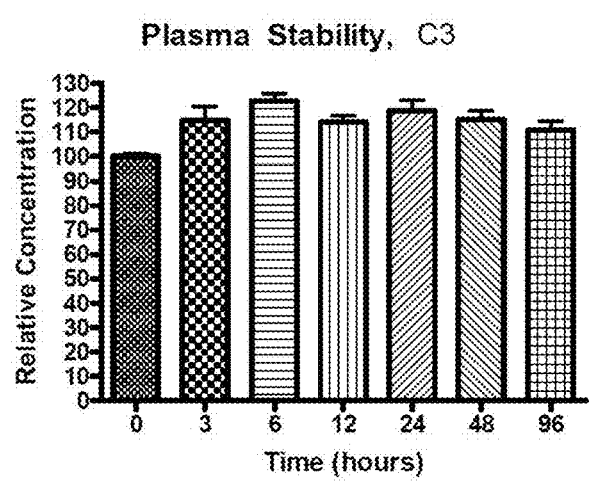
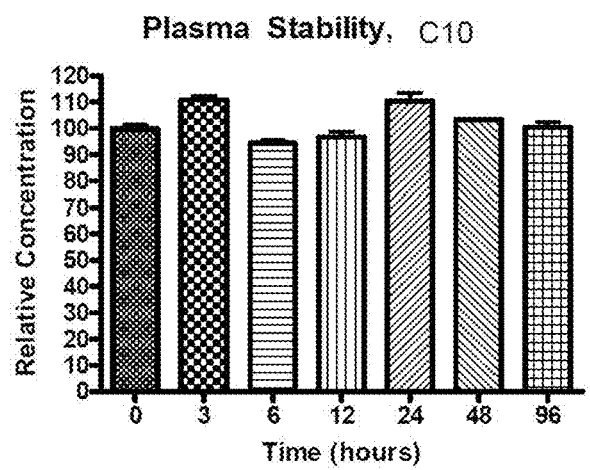

PYRAZOLE DERIVATIVES AS INHIBITORS OF STAT3

CLAIM OF PRIORITY

This application is a continuation of U.S. patent application Ser. No. 14/407,781 (now U.S. Pat. No. 9,732,038), filed Dec. 12, 2014, which is a National Stage application under 35 U.S.C. § 371 of International Application No. PCT/US2013/031227, filed Mar. 14, 2013, which claims the benefit of to U.S. Provisional Patent Application Ser. No. 61/659,924, filed on Jun. 14, 2012, the entire contents of which are hereby incorporated by reference.

TECHNICAL FIELD

This disclosure relates to inhibitors of STAT3 and more particularly to small-molecules such as pyrazole derivatives which are useful in the treatment of diseases related to STAT3 activity.

BACKGROUND

The signal transducer and activator of transcription (STAT) proteins are considered a family of transcriptional factors that are activated in response to growth factors and cytokines and promote cell proliferation and survival (Yu, et al. Crosstalk between cancer and immune cells: role of STAT3 in the tumour microenvironment. Nat Rev Immunol. 2007; 7, 1:41-51). Extracellular signals can activate Janus kinases (JAKs) and receptor tyrosine kinases that in turn activate STATs by phosphorylating a critical tyrosine residue in the active site. A promising location for STAT3 inhibition could be the Src Homology 2 (SH2) domain of STAT3, inhibiting the STAT3 molecule by directly preventing phosphorylation of STAT3, or preventing active phospho-STAT3 homodimer formation. Two phosphorylated STAT monomers are believed to form a homodimer that translocates to the nucleus to bind specific DNA-response elements in the promoters of target genes and induce gene expression (Yu, et al. Enhanced DNA-binding activity of a Stat3-related protein in cells transformed by the Src oncoprotein. Science. 1995; 269, 5220:81-83).

In normal cells, the activation of STAT proteins is very transient and strictly regulated; however, evidence suggests that some STATs may play a key role in oncogenesis (Yu H, Jove R. The STATs of cancer—new molecular targets come of age. Nat Rev Cancer. 2004; 4, 2:97-105). Specifically, STAT3 has been found to be constitutively active in leukemia, lymphoma, breast, and lung and most recently in malignant gliomas (Brantley E, Benveniste E. Signal transducer and activator of transcription-3: a molecular hub for signaling pathways in gliomas. Mol Cancer Res. 2008; 6, 5:675-684; Iwamaru, et al. A novel inhibitor of the STAT3 pathway induces apoptosis in malignant glioma cells both in vitro and in vivo. Oncogene. 2007; 26, 17:2435-2444; Hussain, et al. A novel small molecule inhibitor of signal transducers and activators of transcription 3 reverses immune tolerance in malignant glioma patients. Cancer Res. 2007; 67, 20:9630-9636). Furthermore, inhibition of STAT3 signaling leads to inhibition of cancer cell growth and leads to the induction of apoptosis. STAT3 is believed to mediate tumor-induced immunosuppression at many levels. Activation of STAT3 also mediates propagation of tumor-promoting inflammation and suppression of anti-tumor immunity. Thus, blocking STAT3 activation holds promise for improving cancer treatment by modulating immune responses. (Yu et al., STATs in cancer inflammation and immunity; a leading role for STAT3. Nat Rev Cancer. 2009; 9:798-809)

STAT3 inhibitors exhibit potential as anticancer drugs. Some examples include WP1066, STA21, LLL12, and S31-201. Of these, only a few show good activity in terms of inhibiting STAT3 functions and inhibiting tumor growth in vitro and in vivo. WP1066 has shown more consistent in vitro and in vivo activity in malignant glioma cells. STA-21, the first direct small molecule STAT3 inhibitor, is a natural product with a complex structure that can be synthetically difficult to synthesize. LLL-12, a simplified version of STA-21, shows good inhibition of STAT3 activity both in-vitro and in-vivo and may be considered a potent inhibitor. However, LLL-12 is hard to synthesize with a reported yield of 2.5%; it can also be easily oxidized and therefore not stable, and it is difficult to generate analogs because of the chemistry involved. Various peptides/peptidomimetic compounds have been developed based on the phosphotyrosine sequence of STAT3 or gp130 and show potent STAT3 inhibitory activity. However, significant limitations exist to developing these compounds into drugs due to their peptide nature. There appears to be no evidence that a suitable STAT3 inhibitor is near clinical development.

It is for these shortcomings that new or improved agents which inhibit STAT3, such as pyrazole derivatives, are continually needed for developing new and more effective pharmaceuticals that are aimed at suppression of oncogenesis. The compounds of the invention, as well as their compositions and methods described herein are directed toward these needs and other ends.

SUMMARY

Accordingly, the disclosure provided herein relates to materials and methods for treating, preventing, or ameliorating one or more symptoms, disorders, or conditions associated with STAT3 and their activities. The present invention provides selective inhibitors of STAT3. In one aspect of the disclosure, a composition of matter includes a compound of Formulae I-II:

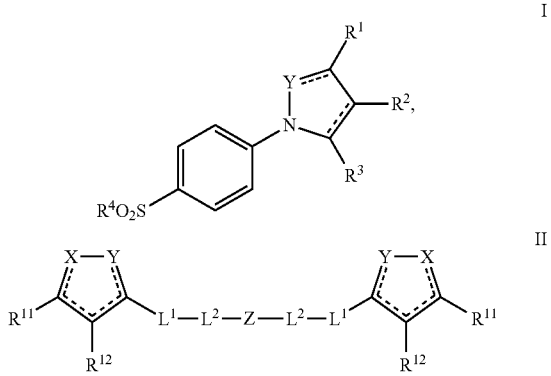

or pharmaceutically acceptable salts thereof, wherein constituent members are defined herein.

The invention further provides a method of modulating (such as, inhibiting) an activity of STAT3 including, contacting STAT3 with a compound of Formulae I-II, or a pharmaceutically acceptable salt thereof.

The invention further provides a method for treating, preventing, or ameliorating one or more symptoms associated with STAT3 including, administering to a subject in need thereof a therapeutically effective amount of a compound of Formulae I-II, or a pharmaceutically acceptable salt thereof.

The invention further provides a method for treating, preventing, or ameliorating one or more STAT3 associated diseases including, administering to a subject in need thereof a therapeutically effective amount of a compound of Formula I-II, or a pharmaceutically acceptable salt thereof.

The invention further provides a method for treating, preventing, or ameliorating one or more symptoms associated with cancer (such as, glioblastoma, medulloblastoma, or human colorectal carcinoma) including, administering to a subject in need thereof a therapeutically effective amount of a compound of Formula I-II, or a pharmaceutically acceptable salt thereof.

The invention further provides a compound of Formulae I-II, or a pharmaceutically acceptable salt thereof, for use in therapy.

The invention further provides a compound of Formulae I-II, or a pharmaceutically acceptable salt thereof, for use in imaging a sample containing STAT3.

The invention further provides use of a compound of Formulae I-II, or a pharmaceutically acceptable salt thereof, for the production of a medicament for use in therapy.

Unless otherwise defined, all technical and scientific terms used herein have the same meaning as commonly understood by one of ordinary skill in the art to which this invention belongs. Although methods and materials similar or equivalent to those described herein can be used in practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 11 is a bar graph showing plasma stability of C6, C3, and C10.

DETAILED DESCRIPTION

Figure 1A:
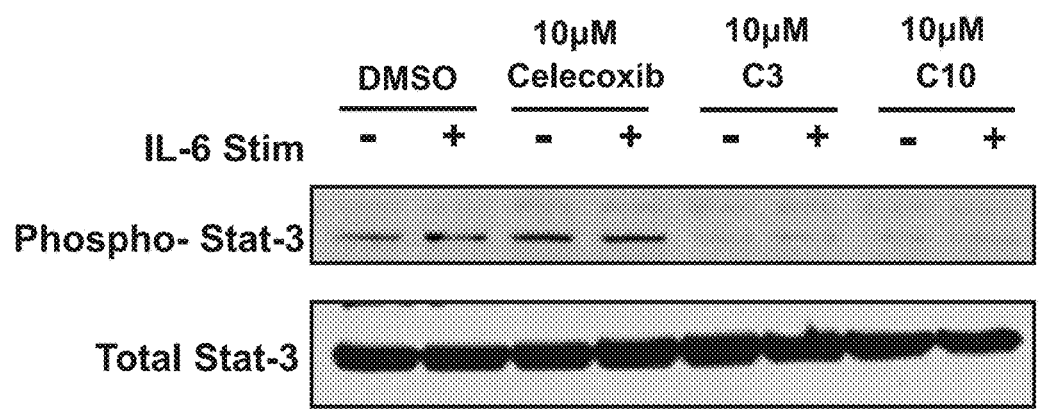
FIG. 1A is an image of Western blot analysis showing constitutive activation of STAT3 phosphorylation in GL261 cells which was blocked by C3 and C10.

The inventions disclosed herein pertain to identification, syntheses, verification and use of a class of small molecules that showed selective inhibition to STAT3. Selective inhibition of STAT3 is expected to result in differential effects on various parameters to be assessed in cell culture and animal models of cancer. These molecules can be used as therapeutics for treating breast cancer, lung cancer, or brain cancer and also as probes for investigating the cellular uptake of STAT3 inhibitors.

A. Definitions

As used herein, pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates.

As used herein, treatment means any manner in which one or more of the symptoms related to a STAT3 activity, e.g., cancer, are ameliorated or otherwise beneficially altered. Treatment also encompasses any pharmaceutical use of the compositions herein, such as uses for treating diseases, disorders, or ailments in which STAT3 is implicated. Treatment may include a decrease in cell proliferation or induction of apoptosis.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $IC_{50}$ refers to an amount, concentration or dosage of a particular test compound that achieves a 50% inhibition of a maximal response in an assay that measures such response.

As used herein, the term $K_i$ represents the dissociation constant of an enzyme/inhibitor complex. It is theoretically independent of the substrate against which the inhibitor is tested. $K_i$ can be calculated from an $IC_{50}$ using the equation: $K_i=IC_{50}*K_m/(S+K_m)$, where S is the concentration of substrate, and $K_m$ is the substrate concentration (in the absence of inhibitor) at which the velocity of the reaction is half-maximal. The $K_i$ of an inhibitor for inhibition of a particular substrate (fixed $K_m$) is constant.

As used herein, $EC_{50}$ refers to a drug concentration that produces 50% of inhibition, and $CC_{50}$ refers to a drug concentration that produces 50% of toxicity.

It is to be understood that the compounds provided herein may contain chiral centers. Such chiral centers may be of either the (R) or (S) configuration, or may be a mixture thereof. In certain cases, particular R and S configurations may be preferred. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic or of either the D- or L-configuration. The designation "d" preceding an amino acid designation (e.g., dAla, dSer, dVal, etc.) refers to the D-isomer of the amino acid. The designation "dl" preceding an amino acid designation refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC), and mass spectrometry (MS), used by those of skill in the art to assess such purity, or sufficiently pure such that further purification would not detectably alter the physical and chemical properties, such as melting point, enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, "alkyl," "alkenyl" and "alkynyl" refer to carbon chains that may be straight or branched. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, vinyl, allyl (propenyl), homoallyl, butadienyl, isoprenyl, ethynyl, and propargyl (propynyl).

As used herein, "cycloalkyl" refers to a saturated or unsaturated, mono- or multicyclic ring system, in certain embodiments of 3 to 10 carbon atoms, in other embodiments of 3 to 6 carbon atoms. The ring systems of the cycloalkyl groups may be composed of one ring or two or more rings which may be joined together in a fused, bridged or spiro-connected fashion. Examples include, but are not limited to, cyclopropyl, cyclobutyl, cyclopentyl, and cyclohexyl.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members, where one or more, in one embodiment 1 to 4, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, "heterocycloalkyl" refers to a monocyclic or multicyclic, saturated or unsaturated ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur.

As used herein, "alkylene," "alkenylene," "alkynylene," "cycloalkylene," "arylene," "heteroarylene," and "heterocycloalkylene" refer to divalent linking "alkyl," "alkenyl," "alkynyl," "cycloalkyl," "aryl," "heteroaryl," and "heterocycloalkyl" groups.

As used herein, "halo", "halogen" or "halide" refers to F, Cl, Br or I.

As used herein, "haloalkyl" refers to an alkyl group in which one or more of the hydrogen atoms are replaced by halogen.

As used herein, "aminoalkyl" refers to —$RNH_2$, in which R is alkyl and the linkage is through a carbon atom.

As used herein, "alkoxy" refers to RO— in which R is alkyl.

As used herein, "alkylamino" refers to RNH—, in which R is alkyl and the linkage is through a nitrogen atom.

As used herein, "dialkylamino" refers to R(R')N—, in which R and R' are the same or different alkyl and the linkage is through a nitrogen atom.

Where the number of any given substituent is not specified (e.g., haloalkyl), there may be one or more substituents present. For example, "haloalkyl" may include one or more of the same or different halogens.

In some embodiments, there are linking substitutents. If not otherwise intended, it intended that these linking substituents comprise both the forwards and backwards forms of the linking moiety, e.g., a CONR linking substituent includes both CONR and NRCO forms.

Unless specified in particular, as used herein, "STAT3" refers to a monomeric, homodimeric, or heterodimeric form of phosphorylated or unphosphorylated STAT3 polypeptide.

As used herein, the abbreviations for any protective groups, amino acids and other compounds, are, unless indicated otherwise, in accord with their common usage, recognized abbreviations, or the IUPAC-IUB Commission on Biochemical Nomenclature (See, (1972) Biochem. 11:942-944).

B. Compositions of Matter

Provided herein are methods and compositions for treating, preventing, or ameliorating one or more symptoms, disorders, or conditions associated with particular STAT3 activity.

In one aspect of the disclosure is provided a compound of Formula I:

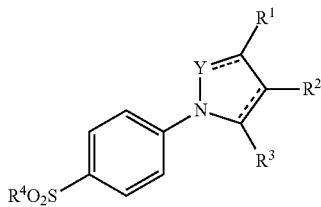

I or a pharmaceutically acceptable salt thereof, wherein:
a dashed line is optionally a bond;
Y is N, O, or S;
$R^1$ and $R^3$ are each independently selected from $C_{1-10}$ alkyl, $C_{2-6}$ alkenyl, $C_{2-6}$ alkynyl, $C_{6-12}$ aryl, $C_{5-12}$ heteroaryl, $C_{3-12}$ cycloalkyl, $C_{3-10}$ heterocycloalkyl, and $(CH_2)_p$—$R^5$, wherein said $C_{1-10}$ alkyl, $C_{2-6}$ alkenyl, $C_{2-6}$ alkynyl, $C_{6-12}$ aryl, $C_{5-12}$ heteroaryl, $C_{3-12}$ cycloalkyl, or $C_{3-10}$ heterocycloalkyl is optionally substituted with 1, 2, 3, 4, or 5 substituents selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)(CH_2)_nO(CH_2)_mC(O)NR^{c1}R^{d1}$, $NR^{c1}C(O)OR^{a1}$, $NR^{c1}C(O)NR^{c1}R^{d1}$, $NR^{c1}S(O)_2R^{b1}$, $S(O)R^{b1}$, $S(O)_2R^{b1}$, and $S(O)_2NR^{c1}R^{d1}$;
$R^2$ is H, $C_{1-10}$ alkyl, or $C_{1-6}$ haloalkyl;
$R^4$ is selected from $NR^{c2}R^{d2}$, $C_{1-10}$ alkyl, $C_{1-6}$ haloalkyl, $C_{2-6}$ alkenyl, $C_{2-6}$ alkynyl, aryl, cycloalkyl, heteroaryl, and heterocycloalkyl, wherein said $C_{1-10}$ alkyl, $C_{2-6}$ alkenyl, $C_{2-6}$ alkynyl, aryl, cycloalkyl, heteroaryl, or heterocycloalkyl is optionally substituted with 1, 2, or 3 substituents independently selected from OH, $C_{1-6}$ alkoxy, CN, amino, alkylamino, dialkylamino, halo, $C_{1-6}$ alkyl, $C_{1-6}$ haloalkyl, aryl, arylalkyl, heteroaryl, heteroarylalkyl, cycloalkyl, and heterocycloalkyl;
$R^5$ is selected from $C_{1-10}$ alkyl, $C_{2-6}$ alkenyl, $C_{2-6}$ alkynyl, $C_{6-12}$ aryl, $C_{5-12}$ heteroaryl, $C_{3-12}$ cycloalkyl, and $C_{3-10}$ heterocycloalkyl, each optionally substituted with 1, 2, 3, 4, or 5 substituents selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)(CH_2)_nO(CH_2)_mC(O)NR^{c1}R^{d1}$, $NR^{c1}C(O)OR^{a1}$, $NR^{c1}C(O)NR^{c1}R^{d1}$, $NR^{c1}S(O)_2R^{b1}$, $S(O)R^{b1}$, $S(O)_2R^{b1}$, and $S(O)_2NR^{c1}R^{d1}$;
$R^{a1}$ is selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;
$R^{b1}$ is selected from H, $C_{1-6}$ alkyl, $C_{1-6}$ haloalkyl, $C_{2-6}$ alkenyl, $C_{2-6}$ alkynyl, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, or 3 substituents independently selected from OH, $C_{1-6}$ alkoxy, CN, amino, alkylamino, dialkylamino, halo, $C_{1-6}$ alkyl, $C_{1-6}$ haloalkyl, aryl, arylalkyl, heteroaryl, heteroarylalkyl, cycloalkyl, and heterocycloalkyl;
$R^{c1}$, $R^{c2}$, $R^{d1}$, and $R^{d2}$ are independently selected from H, $C_{1-6}$ alkyl, $C_{2-6}$ alkenyl, $C_{2-6}$ alkynyl, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, or 3 substituents independently selected from OH, $C_{1-6}$ alkoxy, CN, amino, alkylamino, dialkylamino, halo, $C_{1-6}$ alkyl, $C_{1-6}$ haloalkyl, aryl, arylalkyl, heteroaryl, heteroarylalkyl, cycloalkyl, and heterocycloalkyl; or,
$R^{c1}$ and $R^{d1}$, or $R^{c2}$ and $R^{d2}$, together with the N atom to which they are attached, may optionally form a 4-, 5-, 6-, or 7-membered heterocycloalkyl group or heteroaryl group, each optionally substituted with 1, 2, or 3 substituents independently selected from OH, $C_{1-6}$ alkoxy, CN, amino, alkylamino, dialkylamino, halo, $C_{1-6}$ alkyl, $C_{1-6}$ haloalkyl, aryl, arylalkyl, heteroaryl, heteroarylalkyl, cycloalkyl, and heterocycloalkyl; and,
m, n, and p are independently 1, 2, or 3;
provided that a) when Y is N, $R^1$ is $(CH_2)_p$—$R^5$; and b) when Y is N, p=1, and $R^4$ is $NH_2$, $R^5$ is not F, —OH, —$(CH_2)_2OH$, iso-propyl, $CONH_2$, CN, or —$C_6H_4Me$.

In some embodiments, the dashed line is a bond.
In some embodiments, the dashed line is not a bond.
In some embodiments, Y is N.
In some embodiments, Y is O.
In some embodiments, Y is S.
In some embodiments, $R^1$ is selected from $C_{1-10}$ alkyl, $C_{6-12}$ aryl, $C_{5-12}$ heteroaryl, $C_{3-12}$ cycloalkyl, $C_{3-10}$ heterocycloalkyl, each optionally substituted with 1, 2, 3, 4, or 5 substituents selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)(CH_2)_nO(CH_2)_mC(O)NR^{c1}R^{d1}$, $NR^{c1}C(O)OR^{a1}$, $NR^{c1}C(O)NR^{c1}R^{d1}$, $NR^{c1}S(O)_2R^{b1}$, $S(O)R^{b1}$, $S(O)_2R^{b1}$, and $S(O)_2NR^{c1}R^{d1}$.
In some embodiments, $R^1$ is $C_{1-10}$ alkyl, or $C_{6-12}$ aryl, each optionally substituted with 1, 2, 3, 4, or 5 substituents selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)(CH_2)_nO(CH_2)_mC(O)NR^{c1}R^{d1}$, $NR^{c1}C(O)OR^{a1}$, $NR^{c1}C(O)NR^{c1}R^{d1}$, $NR^{c1}S(O)_2R^{b1}$, $S(O)R^{b1}$, $S(O)_2R^{b1}$, and $S(O)_2NR^{c1}R^{d1}$.
In some embodiments, $R^1$ is $C_{1-10}$ alkyl, or $C_{6-12}$ aryl, each optionally substituted with 1, 2, 3, 4, or 5 substituents selected from $NR^{c1}R^{d1}$, $NR^{c1}C(O)R^{b1}$, $NR^{c1}C(O)(CH_2)_nO(CH_2)_mC(O)NR^{c1}R^{d1}$, $NR^{c1}C(O)OR^{a1}$, $NR^{c1}C(O)NR^{c1}R^{d1}$, and $NR^{c1}S(O)_2R^{b1}$.
In some embodiments, $R^1$ is $(CH_2)_p$—$R^5$.
In some embodiments, $R^2$ is H.
In some embodiments, $R^3$ is selected from $C_{6-12}$ aryl, $C_{5-12}$ heteroaryl, $C_{3-12}$ cycloalkyl, and $C_{3-10}$ heterocycloalkyl, each optionally substituted with 1, 2, 3, 4, or 5 substituents selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^1S(O)_2R^{b1}$, $S(O)R^{b1}$, $S(O)_2R^{b1}$, and $S(O)_2NR^{c1}R^{d1}$.

In some embodiments, $R^3$ is selected from $C_{6-12}$ aryl, $C_{5-12}$ heteroaryl, $C_{3-12}$ cycloalkyl, and $C_{3-10}$ heterocycloalkyl, each optionally substituted with 1, 2, 3, 4, or 5 substituents selected from $C_{1-6}$ alkyl, $C_{1-6}$ haloalkyl, halo, and CN.

In some embodiments, $R^3$ is selected from $C_{6-12}$ aryl optionally substituted with 1, 2, or 3 substituents selected from $C_{1-6}$ alkyl, $C_{1-6}$ haloalkyl, halo, and CN.

In some embodiments, $R^3$ is $(CH_2)_p-R^5$.

In some embodiments, $R^4$ is selected from $NR^{c2}R^{d2}$, $C_{1-10}$ alkyl, and $C_{1-6}$ haloalkyl.

In some embodiments, $R^5$ is selected from $C_{1-10}$ alkyl, $C_{6-12}$ aryl, $C_{5-12}$ heteroaryl, $C_{3-12}$ cycloalkyl, $C_{3-10}$ heterocycloalkyl, each optionally substituted with 1, 2, 3, 4, or 5 substituents selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)(CH_2)_nO(CH_2)_mC(O)NR^{c1}R^{d1}$, $NR^{c1}C(O)OR^{a1}$, $NR^{c1}C(O)NR^{c1}R^{d1}$, $NR^{c1}S(O)_2R^{b1}$, $S(O)R^{b1}$, $S(O)_2R^{b1}$, and $S(O)_2NR^{c1}R^{d1}$.

In some embodiments, $R^5$ is $C_{1-10}$ alkyl, or $C_{6-12}$ aryl, each optionally substituted with 1, 2, 3, 4, or 5 substituents selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)(CH_2)_nO(CH_2)_mC(O)NR^{c1}R^{d1}$, $NR^{c1}C(O)OR^{a1}$, $NR^{c1}C(O)NR^{c1}R^{d1}$, $NR^{c1}S(O)_2R^{b1}$, $S(O)R^{b1}$, $S(O)_2R^{b1}$, and $S(O)_2NR^{c1}R^{d1}$.

In some embodiments, $R^5$ is $C_{1-10}$ alkyl, or $C_{6-12}$ aryl, each optionally substituted with 1, 2, 3, 4, or 5 substituents selected from $NR^{c1}R^{d1}$, $NR^{c1}C(O)R^{b1}$, $NR^{c1}C(O)(CH_2)_nO(CH_2)_mC(O)NR^{c1}R^{d1}$, $NR^{c1}C(O)OR^{a1}$, $NR^{c1}C(O)NR^{c1}R^{d1}$, and $NR^{c1}S(O)_2R^{b1}$.

In some embodiments, the compound has a Formula IA or IB:

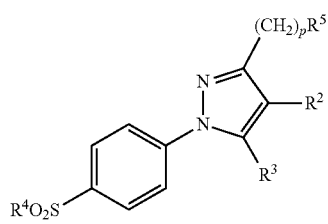

IA

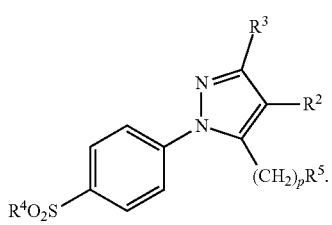

IB

In some embodiments, the compound has a Formula IC or ID:

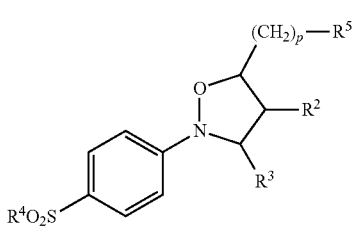

IC

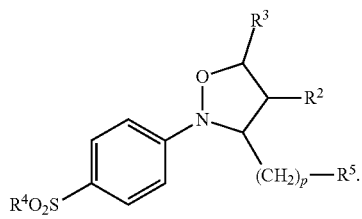

ID

In another aspect of the disclosure is provided a compound of Formula II,

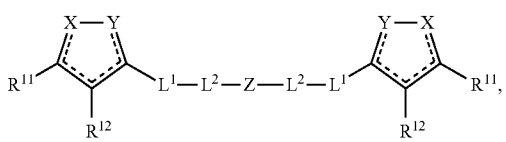

II or a pharmaceutically acceptable salt thereof, wherein:

each $R^{11}$ is independently selected from $C_{1-10}$ alkyl, $C_{2-6}$ alkenyl, $C_{2-6}$ alkynyl, $C_{6-12}$ aryl, $C_{5-12}$ heteroaryl, $C_{3-12}$ cycloalkyl, and $C_{3-10}$ heterocycloalkyl, heterocycloalkylalkyl, arylalkyl, and heteroarylalkyl, each optionally substituted with 1, 2, 3, 4, or 5 substituents selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)(CH_2)_nO(CH_2)_mC(O)NR^{c1}R^{d1}$, $NR^{c1}C(O)OR^{a1}$, $NR^{c1}C(O)NR^{c1}R^{d1}$, $NR^{c1}S(O)_2R^{b1}$, $S(O)R^{b1}$, $S(O)_2R^{b1}$, and $S(O)_2NR^{c1}R^{d1}$;

each $R^{12}$ is independently H, $C_{1-10}$ alkyl, or $C_{1-6}$ haloalkyl;

X is N and Y is $N-C_6H_4SO_2R^4$; or
X is $N-C_6H_4SO_2R^4$ and Y is N;

each $L^1$ is $-W^1-W^2-$;

$W^1$ and $W^2$ are independently absent or independently a divalent moiety selected from $C_{1-6}$ alkylene, arylene, cycloalkylene, heteroarylene or heterocycloalkylene, each optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino;

each $L^2$ is $-W^3-W^4-W^5-W^6-W^7$;

$W^3$, $W^4$, $W^5$, $W^6$, and $W^7$ are independently absent or independently selected from $C_{1-6}$ alkylene, arylene, cycloalkylene, heteroarylene, and heterocycloalkylene, O, S, $NR^h$, CO, COO, $CONR^h$, SO, $SO_2$, $SONR^h$, and $NR^h$-$CONR^i$ wherein each of the $C_{1-6}$ alkylene, arylene, cycloalkylene, heteroarylene, and heterocycloalkylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

Z is selected from $C_{1-10}$ alkylene, O, S, and $NR^h$;

$R^4$ is selected from $NR^{c2}R^{d2}$, $C_{1-10}$ alkyl, $C_{1-6}$ haloalkyl, $C_{2-6}$ alkenyl, $C_{2-6}$ alkynyl, aryl, cycloalkyl, heteroaryl, and heterocycloalkyl, wherein said $C_{1-10}$ alkyl, $C_{2-6}$ alkenyl, $C_{2-6}$ alkynyl, aryl, cycloalkyl, heteroaryl, or heterocycloalkyl is optionally substituted with 1, 2, or 3 substituents independently selected from OH, $C_{1-6}$ alkoxy, CN, amino, alkylamino, dialkylamino, halo, $C_{1-6}$ alkyl, $C_{1-6}$ haloalkyl, aryl, arylalkyl, heteroaryl, heteroarylalkyl, cycloalkyl, and heterocycloalkyl;

$R^{a1}$ is selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{b1}$ is selected from H, $C_{1-6}$ alkyl, $C_{1-6}$ haloalkyl, $C_{2-6}$ alkenyl, $C_{2-6}$ alkynyl, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, or 3 substituents independently selected from OH, $C_{1-6}$ alkoxy, CN, amino, alkylamino, dialkylamino, halo, $C_{1-6}$ alkyl, $C_{1-6}$ haloalkyl, aryl, arylalkyl, heteroaryl, heteroarylalkyl, cycloalkyl, and heterocycloalkyl;

$R^{c1}$, $R^{c2}$, $R^{d1}$, and $R^{d2}$ are independently selected from H, $C_{1-6}$ alkyl, $C_{2-6}$ alkenyl, $C_{2-6}$ alkynyl, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, or 3 substituents independently selected from OH, $C_{1-6}$ alkoxy, CN, amino, alkylamino, dialkylamino, halo, $C_{1-6}$ alkyl, $C_{1-6}$ haloalkyl, aryl, arylalkyl, heteroaryl, heteroarylalkyl, cycloalkyl, and heterocycloalkyl; or, $R^{c1}$ and $R^{d1}$, or $R^{c2}$ and $R^{d2}$, together with the N atom to which they are attached, may optionally form a 4-, 5-, 6-, or 7-membered heterocycloalkyl group or heteroaryl group, each optionally substituted with 1, 2, or 3 substituents independently selected from OH, $C_{1-6}$ alkoxy, CN, amino, alkylamino, dialkylamino, halo, $C_{1-6}$ alkyl, $C_{1-6}$ haloalkyl, aryl, arylalkyl, heteroaryl, heteroarylalkyl, cycloalkyl, and heterocycloalkyl;

$R^h$ and $R^i$ are independently selected from H and $C_{1-6}$ alkyl; and, m and n are independently 1, 2, or 3.

In some embodiments, $R^{11}$ is $C_{6-12}$ aryl optionally substituted with 1, 2, 3, 4, or 5 substituents selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)(CH_2)_nO(CH_2)_mC(O)NR^{c1}R^{d1}$, $NR^{c1}C(O)OR^{a1}$, $NR^{c1}C(O)NR^{c1}R^{d1}$, $NR^{c1}S(O)_2R^{b1}$, $S(O)R^{b1}$, $S(O)_2R^{b1}$, and $S(O)_2NR^{c1}R^{d1}$.

In some embodiments, $R^{11}$ is $C_{6-12}$ aryl optionally substituted with 1 or 2 substituents selected from halo, CN.

In some embodiments, $R^{12}$ is H.

In some embodiments, $W^1$ and $W^2$ are independently $C_{1-6}$ alkylene or arylene, each optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino.

In some embodiments, $W^3$ and $W^6$ are $CONR^h$, $W^4$ and $W^6$ are $C_{1-6}$ alkylene, and $W^5$ is O.

In some embodiments, Z is $C_{1-10}$ alkylene.

In some embodiments, the compound is selected from:

3-(4-Aminobenzyl)-5-(4-bromophenyl)-1-(4-aminosulfonylphenyl)-1H-pyrazole (C1);

3-(4-Aminobenzyl)-5-phenyl-1-(4-aminosulfonylphenyl)-1H-pyrazole (C2);

3-[{2-[(Methylaminocarbonyl)-methoxy]-acetyl}-(4-aminobenzyl)]-5-(4-bromophenyl)-1-(4-aminosulfonylphenyl)-1H-pyrazole (C3);

3-(4-Acetamidebenzyl)-5-(4-bromophenyl)-1-(4-aminosulfonylphenyl)-1H-pyrazole (C4);

3-(4-Benzamide-benzyl)-5-(4-bromophenyl)-1-(4-aminosulfonylphenyl)-1H-pyrazole (C5);

5-(4-Bromophenyl)-3-(isopentyl)-1-(4-aminosulfonylphenyl)-1H-pyrazole (C6);

3-(4-Bromophenyl)-5-(isopentyl)-1-(4-aminosulfonylphenyl)-1H-pyrazole (C7);

5-phenyl-3-(isopentyl)-1-(4-aminosulfonylphenyl)-1H-pyrazole (C8); and 3-(Phenyl)-5-(isopentyl)-1-(4-aminosulfonylphenyl)-1H-pyrazole (C9), or a pharmaceutically acceptable salt thereof.

In some embodiments, the compound is 3-[{2-[(7-{2-[((4-((5-(4-Bromophenyl)-1-(4-sulfamoylphenyl)-1H-pyrazol-3-yl)methyl)phenyl)aminocarbonyl)-methoxy]-acetylamino}-heptylaminocarbonyl)-methoxy]-acetyl}-(4-aminobenzyl)]-5-(4-bromophenyl)-1-(4-aminosulfonylphenyl)-1H-pyrazole (C10) or a pharmaceutically acceptable salt thereof.

C. Preparation of the Compounds

The compounds of the present invention can be prepared in a variety of ways known to one skilled in the art of synthetic organic chemistry or by the methods described herein. In addition, certain variations to the procedures with respect to reaction conditions such as stoichiometry, solvents, reagents, catalysts, and temperatures; work-up; and purification conditions described below will be recognized by one skilled in the art. Preparation of the compounds can involve a temporary protection and deprotection of reactive chemical groups. The chemistry of protecting groups can be found in Wuts and Greene, *Greene's Protective Groups in Organic Synthesis*, 4*th* Ed., Wiley & Sons: New York, 2006.

The compounds of the invention can be prepared, for example, by the Schemes 1-5 shown below.

Scheme 1.

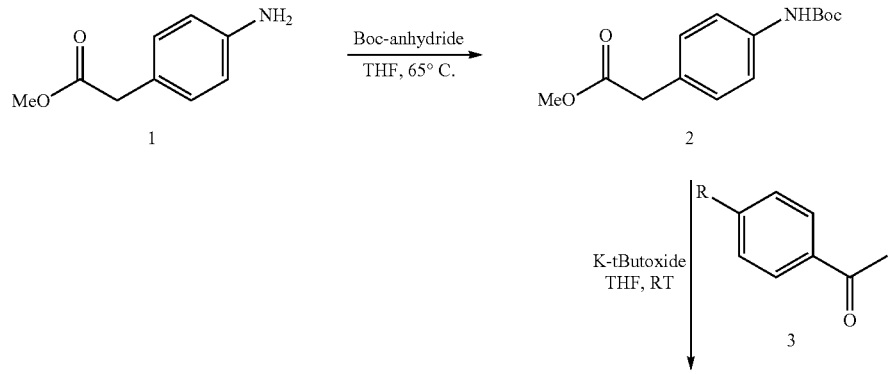

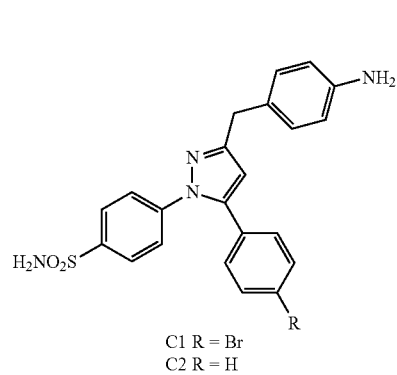

C1 R = Br
C2 R = H

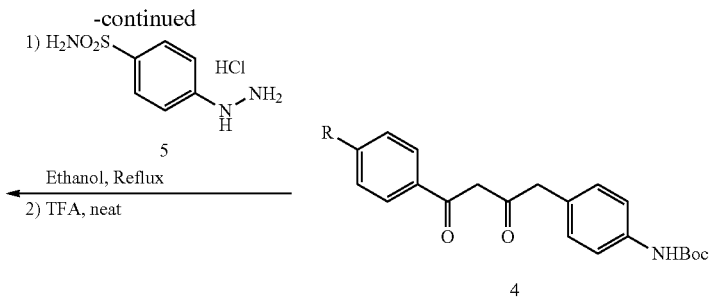

The amine 1 can be treated with Boc-anhydride to form the protected amine 2 which can be condensed with an acetophenone, such as, 3 to provide a 1,3-dione 4. The diones, such as, 4 can react with hydrazines, such as, 5 followed by deprotection of the Boc-group to provide pyrazoles, such as, C1 or C2.

The pyrazoles, such as C1 can be derivatized with acids, acid anhydrides, acid chlorides, or other acetylating agents as shown, for example, in Scheme 2. In this scheme, the acid 9 was coupled with the pyrazole C1 to provide the amide C3.

Scheme 2.

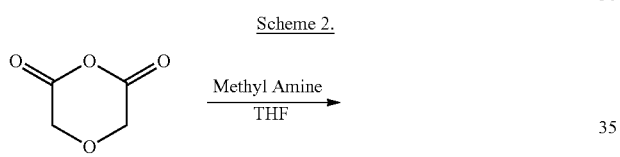

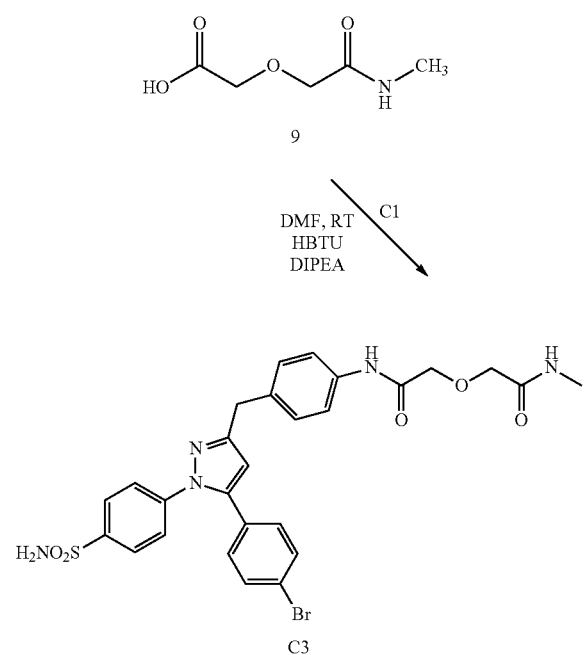

The aryl NH$_2$ of the pyrazole can be treated with acetyl or benzoyl chloride (See, Scheme 3) using standard protocols to provide compounds such as C4 and C5.

Scheme 3.

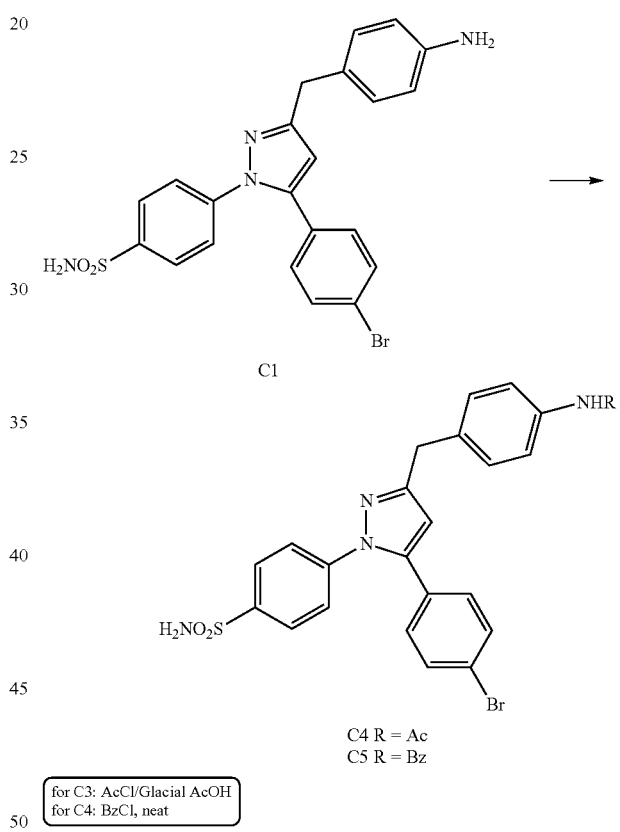

C4 R = Ac
C5 R = Bz for C3: AcCl/Glacial AcOH
for C4: BzCl, neat

Scheme 4 shows the reaction of another dione 10, which has an alkyl and an aryl group at the two carbonyls with the hydrazine 5 to form pyrazoles. In this reaction, two isomeric pyrazoles, the 1,5-diaryl pyrazole C6 and the 1,3-diaryl pyrazole C7 were obtained depending on the direction of addition of the hydrazines. These two components were separated and analyzed. Similar isomeric pyrazoles C8 and C9 were obtained when R=H. C7 and C9 show strong ultraviolet fluorescence, while the C6 and C8 isomers do not. C9 has maximal UV absorption at 285 nm and maximal emission at 400 nm. While not intending to be bound by any particular theory, two-dimensional NMR spectroscopy and modeling experiments predict the three aromatic rings of the 1,3-diaryl derivatives to be in a planar configuration while the phenyl rings of the 1,5-diaryl derivatives are tilted out of the pyrazole plane to maximize distance between aromatic hydrogens on adjacent rings. The pi overlap created by the planar configuration of the 1,3 diaryl derivatives likely lead to their fluorescent properties.

Scheme 4.

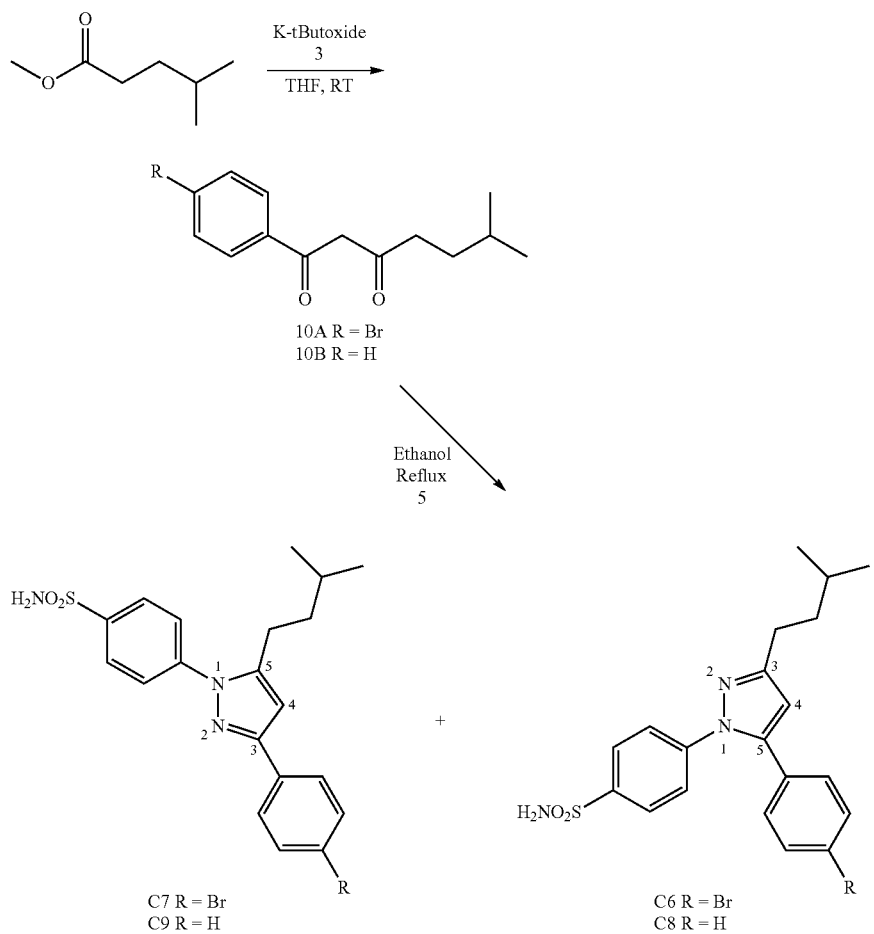

For the bivalent compounds, the symmetrical spacers can be readily prepared by condensation of two equivalents of diglycolic anhydride with one equivalent of the appropriate alkyl diamine, such as, 7 to give the biscarboxylic acid derivatives 8 in nearly quantitatively yield. Subsequent coupling of 2 equivalents of C1 with the biscarboxylic acids 8 using HBTU afforded the bivalent ligands, such as, C10 (~50% yield).

Scheme 5.

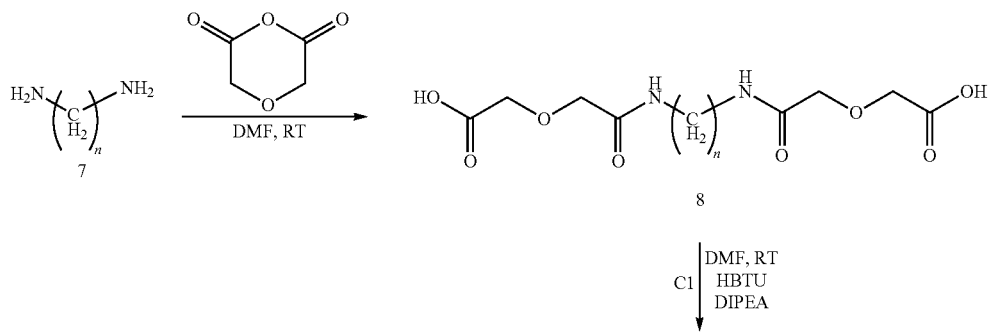

-continued

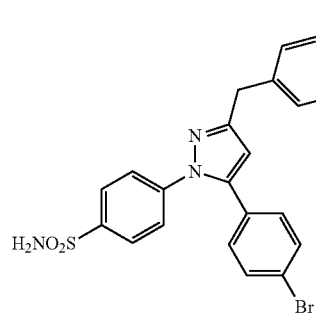 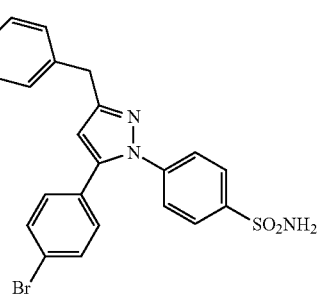

C10 n = 7

The compounds of the invention were characterized using standard techniques such as nuclear magnetic resonance (NMR), MS including LRMS and HPLC.

D. Formulation of Pharmaceutical Compositions

The pharmaceutical compositions provided herein contain therapeutically effective amounts of one or more of the compounds provided herein that are useful in the treatment, prevention, or amelioration of one or more of the symptoms associated with STAT3 activity, or a disorder, condition, or ailment in which STAT3 activity (e.g., glioblastoma, medulloblastoma, or human colorectal carcinoma) is implicated, and a pharmaceutically acceptable carrier. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. For example, the compounds may be formulated or combined with known NSAIDs, anti-inflammatory compounds, steroids, and/or antibiotics.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (See, e.g., Ansel, Introduction to Pharmaceutical Dosage Forms, 4th Edition, 1985, 126).

In the compositions, effective concentration(s) of one or more compounds or pharmaceutically acceptable salts thereof is (are) mixed with a suitable pharmaceutical carrier. The concentrations of the compounds in the compositions are effective for delivery of an amount, upon administration, that treats, prevents, or ameliorates one or more of the symptoms of STAT3 activity.

In one embodiment, the compositions are formulated for single dosage administration. To formulate a composition, the weight fraction of compound is dissolved, suspended, dispersed or otherwise mixed in a selected carrier at an effective concentration such that the treated condition is relieved or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro, ex vivo and in vivo systems, and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disorder being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable salts thereof. The pharmaceutically therapeutically active compounds and salts thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, See Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, or in one embodiment 0.1-95%.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol, and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or a pharmaceutically acceptable salt thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action. The active ingredient is a compound or pharmaceutically acceptable salt thereof as described herein. Higher concentrations, up to about 98% by weight of the active ingredient, may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

2. Injectables, Solutions, and Emulsions

Parenteral administration, in one embodiment characterized by injection, either subcutaneously, intramuscularly, intravenously, or intra-arterially is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (See, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous, intra-arterial, and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include sodium chloride injection, ringers injection, isotonic dextrose injection, sterile water injection, dextrose and lactated ringers injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration should be sterile, as is known and practiced in the art.

Illustratively, intravenous or intra-arterial infusion of a sterile aqueous solution containing an active compound is an effective mode of administration. Another embodiment is a sterile aqueous or oily solution or suspension containing an active material injected as necessary to produce the desired pharmacological effect.

The present invention includes formulation of the compounds for intra-arterial administration as is conventional in the art, as described in, for example, Boockvar et al., Safety and maximum tolerated dose of superselective intraarterial cerebral infusion of bevacizumab after osmotic blood-brain barrier disruption for recurrent malignant glioma, J. Neurosurg. 114:624-632 (2011), with or without accompanying blood brain barrier disruption ("BBBD"), and with or without occlusion. Briefly, where compounds of the invention are administered intra-arterially with occlusion, primary arteries leading to the target site are catheterized and the compounds are administered through a catheter. Embolization of the arteries, in order to retain the compounds at the target site for a longer period, is performed using polyvinyl alcohol particles alone or in combination with coils. The compounds of the invention herein can be dissolved in saline prior to intra-arterial injection and such injection may be preceded by heparin treatment and sedation. For safest treatment of brain tumor, preferably, intra-arterial administration is conducted before tumor burden becomes excessive. Intra-arterial delivery of the agents herein may be followed by osmotic disruption of the blood brain barrier ("BBB") as conventional in the art. The increased transfer of drugs into the central nervous system ("CNS") can thus be accomplished, preferably just prior to intra-arterial delivery. For such disruption, a catheter is placed into an artery, usually the superficial temporal artery, leading to the brain and the BBB is disrupted with a solution of mannitol. This invasive procedure is typically performed while the patient is under general anesthesia. Such treatment may require prior hydration and administration of anticonvulsants and/or atropine.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle.

The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable salts thereof may be formulated as aerosols for topical application, such as by inhalation (See, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as transdermal patches, including iotophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (*theobroma oil*), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 g.

Tablets and capsules for rectal administration are manufactured using the same pharmaceutically acceptable substance and by the same methods as for formulations for oral administration.

6. Targeted Formulations

The compounds provided herein, or pharmaceutically acceptable salts thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, See, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline (PBS) lacking divalent cations is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable salts may be packaged as articles of manufacture (e.g., kits) containing packaging material, a compound or pharmaceutically acceptable salt thereof provided herein within the packaging material, and a label that indicates that the compound or composition, or pharmaceutically acceptable salt thereof, is useful for treatment, prevention, or amelioration of one or more symptoms or disorders in which STAT3 activity, including cancer is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252.

Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

8. Sustained Release Formulations

Also provided are sustained release formulations to deliver the compounds to the desired target at high circulating levels (between $10^{-9}$ and $10^{-4}$ M). The levels are either circulating in the patient systemically, or in one embodiment, localized to a site of, e.g., paralysis.

It is understood that the compound levels are maintained over a certain period of time as is desired and can be easily determined by one skilled in the art. Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein may be readily selected for use with the pharmaceutical compositions provided herein. Thus, single unit dosage forms suitable for oral administration, such as, but not limited to, tablets, capsules, gelcaps, caplets, powders and the like, that are adapted for sustained release are contemplated herein.

In one embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are contemplated herein. The sustained release formulation is encapsulated by coating particles or granules of the pharmaceutical compositions provided herein with varying thickness of slowly soluble polymers or by microencapsulation. In one embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, in one embodiment 20 to 25%, and the amount of coating will be from 10 to 25% of the weight of the active material, and in another embodiment, 15 to 20% of the weight of active material. Any conventional pharmaceutically acceptable plasticizer may be incorporated into the coating.

The compounds provided herein can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations provided herein are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds.

Preparations for oral administration may be suitably formulated to give controlled release of the active compound. In one embodiment, the compounds are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compositions provided herein may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, *arachis*, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and nontoxic, include but are not limited to hydrogels, silicones, polyethylenes, ethylene-vinyl acetate copolymers, or biodegradable polymers.

E. Evaluation of the Activity of the Compounds

The activity of the compounds provided herein as inhibitors of STAT3 activity may be measured in standard assays, e.g., X-ray crystallographic analysis of inhibitor-bound STAT3 complexes, enzymatic inhibition assays, cell cytoprotection and viability assays (as described below).

All molecular models were made using the Discovery Studio platform (version 2.5, from Accelrys) at the Minnesota Supercomputing Institute (MSI, University of Minnesota, Twin Cities campus). Three dimensional molecular models of STAT3 homodimers were constructed using the available X-ray crystal structure [entry 1BG1 in the Protein Data Bank (www.pdb.org)]. Preliminary modeling results of the STAT3-Src Homology 2 (SH2) domain revealed three binding subpockets: two hydrophobic sites surrounding a hydrophilic phosphate-recognition site. The pTyr705 binding pocket is believed to be polar and basic and is characteristic for a phosphotyrosine SH2 domain. The binding pocket for the Leu706 side chain is believed to be very hydrophobic as is the nearby side pocket that the upstream peptide chain traverses (side pocket). A successful inhibitor will likely contain a phosphomimetic and utilize all three binding subpockets. Blocking the SH2 binding pocket with a small molecule will likely inhibit the activation of the STAT3 homodimer complex and potentially be a promising therapeutic approach for the treatment of cancers that use STAT3 signaling.

Using molecular modeling techniques, Li and coworkers predicted the FDA approved COX-2 inhibitor, celecoxib, could bind to the SH2 domain of STAT3. (Li, et al. Fragment-Based Drug Design and Drug Repositioning Using Multiple Ligand Simultaneous Docking (MLSD): Identifying Celecoxib and Template Compounds as Novel Inhibitors of Signal Transducer and Activator of Transcription 3 (STAT3). Journal of medicinal chemistry. Aug. 11, 2011; 54, 15:5592-5596). According to their modeling studies, the phenylsulfonamide group of celecoxib occupied the pTyr705 site and the phenylmethyl group projected into the side pocket. They also showed that celecoxib inhibited STAT3 phosphorylation in two cancer cell lines and has an $IC_{50}$ of 43 µM in a cell viability assay.

The central pyrazole core of celecoxib is potentially suitable for designing STAT3 SH2 domain inhibitors because its trisubstituted side chains can interact with the three binding subpockets of STAT3. The retention of celecoxib's COX-2 activity required a trifluoro substituent or similar in the $3^{rd}$ position of the pyrazole ring. Accordingly, removing this group to enhance STAT3 binding could render these compounds devoid of COX2 activity. Small molecule compounds such as Formulae I-II can bind monovalently to STAT3 (such as phosphorylated or unphosphorylated STAT3).

Another approach for binding to STAT3 proteins is through bivalent ligands which could either bind to a monomeric STAT3 (such as phosphorylated or unphosphorylated STAT3) or to two molecules of STAT3 protein (such as phosphorylated or unphosphorylated STAT3). The key binding pocket is belived to be the the SH2 domain of one monomer that interacts with the phosphotyrosine peptide sequence [Pro-pTyr-Leu-Lys-Thr-Lys] of the other monomer forming reciprocal homodimer interactions. This structure could be suitable for designing a ligand that will bind bivalently to both SH2 domains. Modeling studies have shown the distance between the phospho-tyrosine binding sites is about 42 Angstroms. Thus, a bivalent ligand with a spacer that will accommodate this distance could help bind both domains. In a dimeric system such as the STAT3 homodimer, a bivalent ligand with an optimal length spacer could exhibit enhanced binding over an equivalent monovalent ligand. While not intending to be bound by any particular theory, it is believed that a bivalent ligand would first bind univalently followed by binding of the second pharmacophore to the neighboring receptor. Bridging would be favored over a second ligand binding univalently because of the close proximity (high "effective" concentration) of the tethered pharmacophore.

The bivalent ligands that may span the two SH2 binding pockets of the STAT3 homodimer represents a novel approach that has not been tried for STAT3 and likely lead to compounds that are more specific and selective for inhibiting STAT3. Additionally, bivalent ligands may be useful tools to further characterize STAT signaling.

Compounds described herein can bind to the SH2 domain of STAT3 and inhibit the STAT3 phosphorylation. Compounds described herein can also prevent the dimerization of STAT3. Such inhibition can lead to inhibition of STAT3 dimer binding to the DNA and hence to inhibit the STAT3 dependent transcriptional activity (such as of proliferation proteins or anti-apoptopic proteins).

Figure 1B:
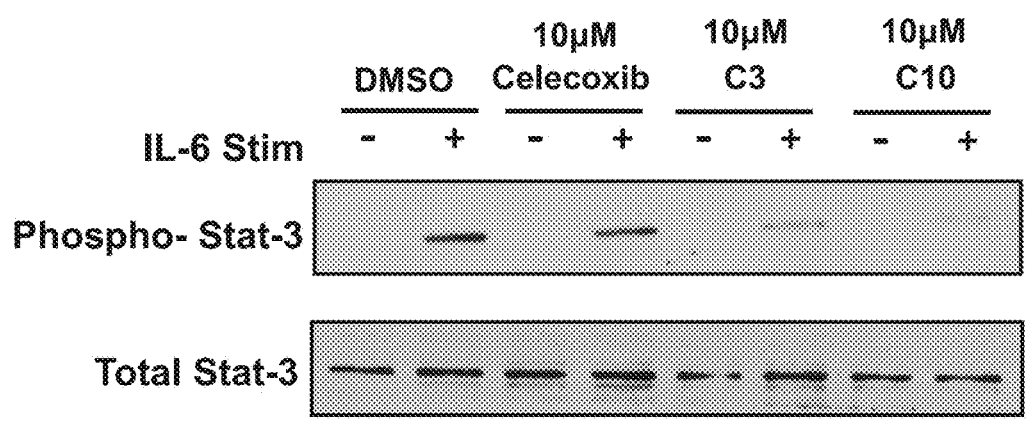
FIG. 1B is an image of Western blot analysis showing constitutive activation of STAT3 phosphorylation in dBT114 cells which was blocked by C3 and C10.
Figure 2:
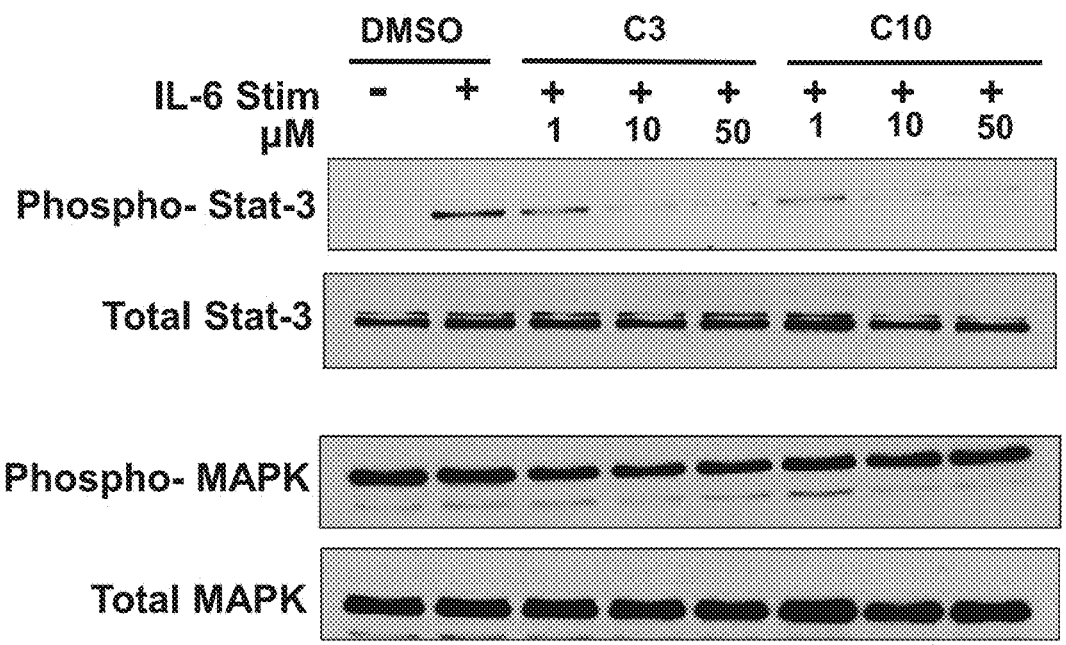
FIG. 2 is an image showing dose-dependent inhibition of STAT3 phosphorylation in dBT114 cells by C3 and C10 with no effect on MAP Kinase levels.

Compounds described herein can be tested for blocking the activation of phospho-STAT3 in vitro. Interleukin-6 (IL-6) leads to potent activation of STAT3, especially in cells that do not express persistently phosphorylated STAT3. The compounds were tested for inhibiting IL-6 induced phosphorylation of STAT3 in a human Glioblastoma GBM stem cell line (dBT114) and in the murine GBM cell line, GL261. IL-6 potently activates STAT3 phosphorylation in dBT114 cells but not as much in GL261 cells (FIG. 1), showing that GL261 cells have constitutively activated STAT3. C3 and C10 potently inhibited STAT3 phosphorylation at 10 µM, while celecoxib had no effect at that dose in either tumor cell lines (FIG. 1). A dose dependent decrease of IL-6 induced STAT3 phosphorylation in dBT114 cells using increasing concentrations of our compounds was observed, while no effect was seen on the levels of activated MAP kinase (FIG. 2).

Figure 3:
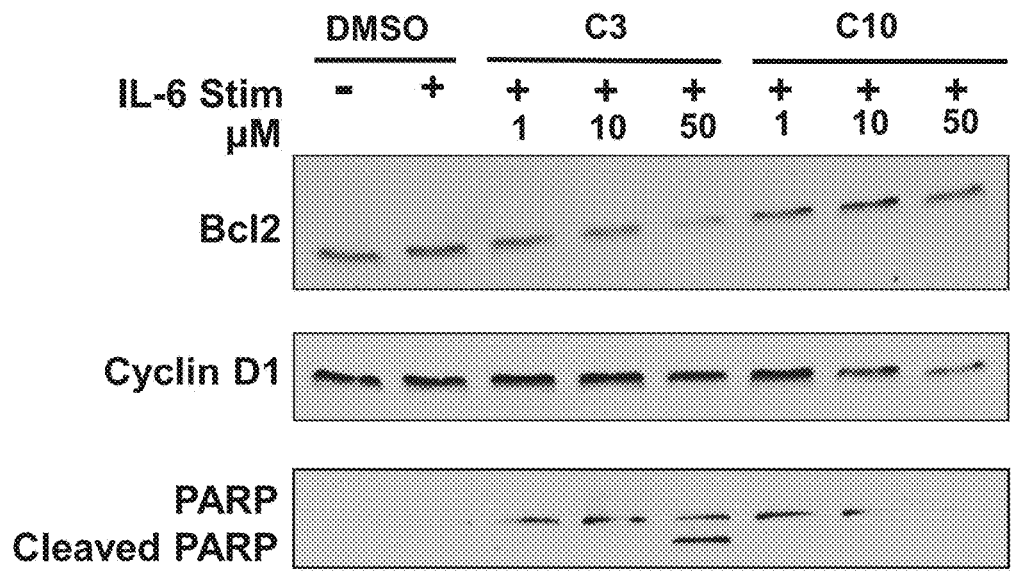
FIG. 3 is an image showing the effect of C3 and C10 on Bcl-2, Cyclin D1, and PARP protein levels.

STAT3 is a transcription factor that leads to the activation of several pro-proliferation proteins including Cyclin D1 and numerous anti-apoptotic proteins such as Bcl-2. To analyze the effects on the downstream targets of STAT3 transcription, Cyclin D1 and Bcl-2 protein levels were monitored after exposure to the compounds described. dBT114 cells were treated with various concentrations of C3, C10 or DMSO for 24 hours. We found that C3 decreased Bcl-2 in a dose dependent fashion, while C10 decreased Cyclin D1 levels in a dose dependent fashion. Inhibition of STAT3 signaling by C3 also leads to the induction of apoptosis as evidenced by the cleavage of PARP (FIG. 3).

Figure 4A:
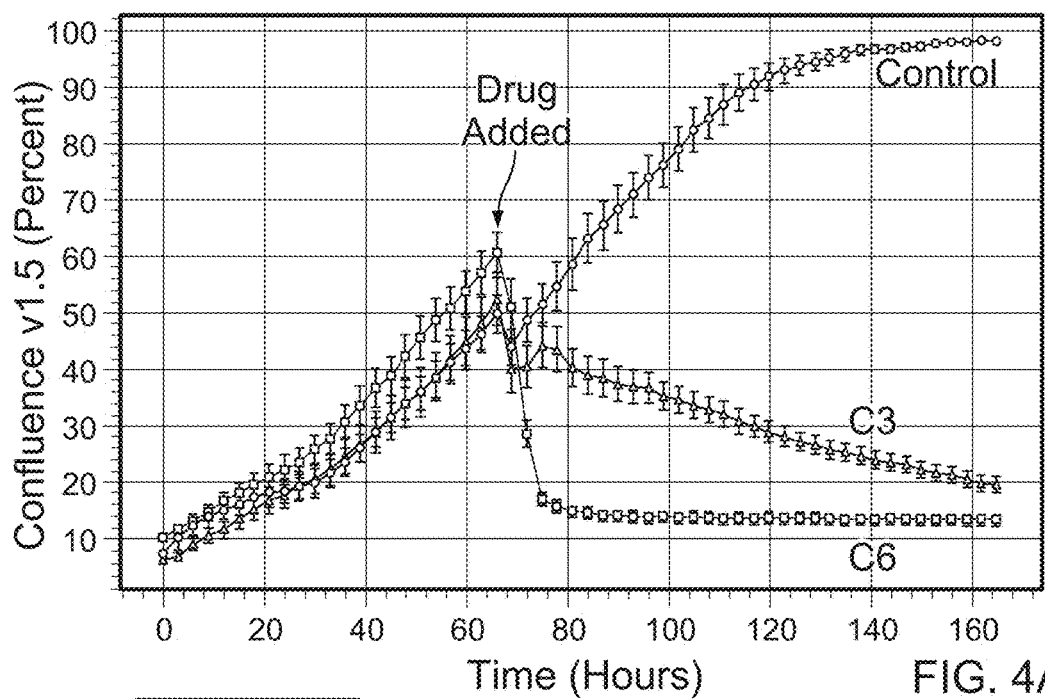
FIG. 4A is a line graph of confluence measurements upon addition of DMSO, C3, and C6 in glioblastoma (dBT114) cell line.
Figure 4B:
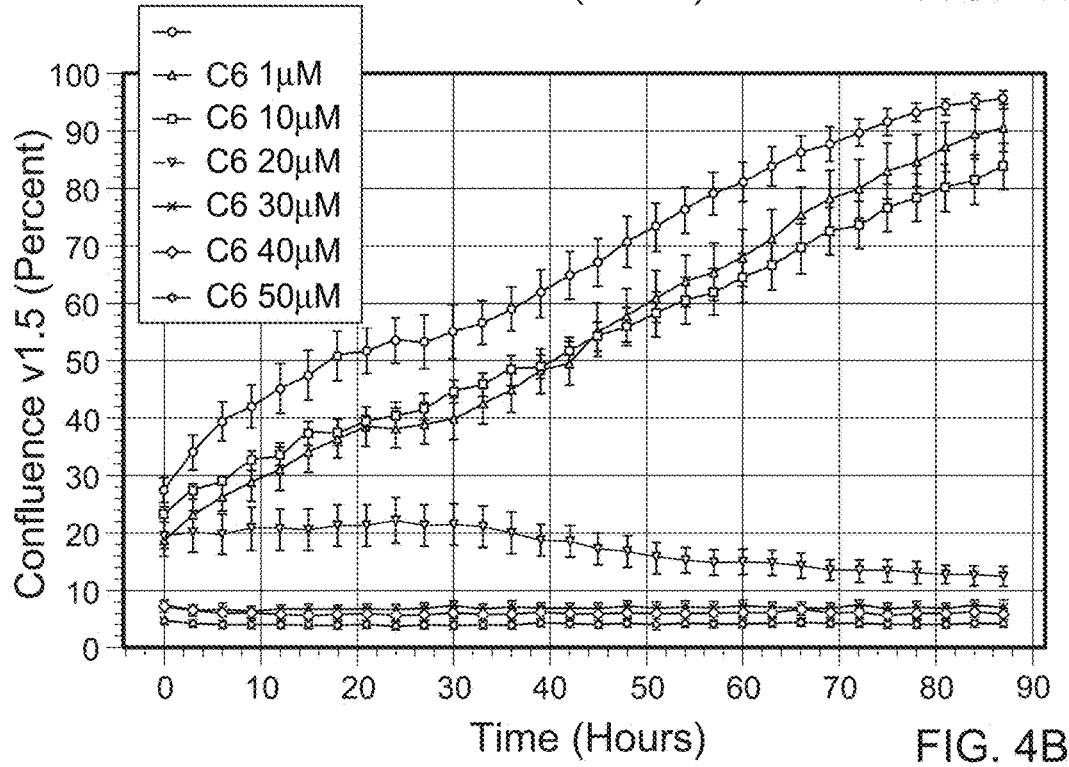
FIG. 4B is a line graph of confluence measurements in dose dependent inhibition by C6 in glioblastoma (dBT114) cell line.
Figure 5A:
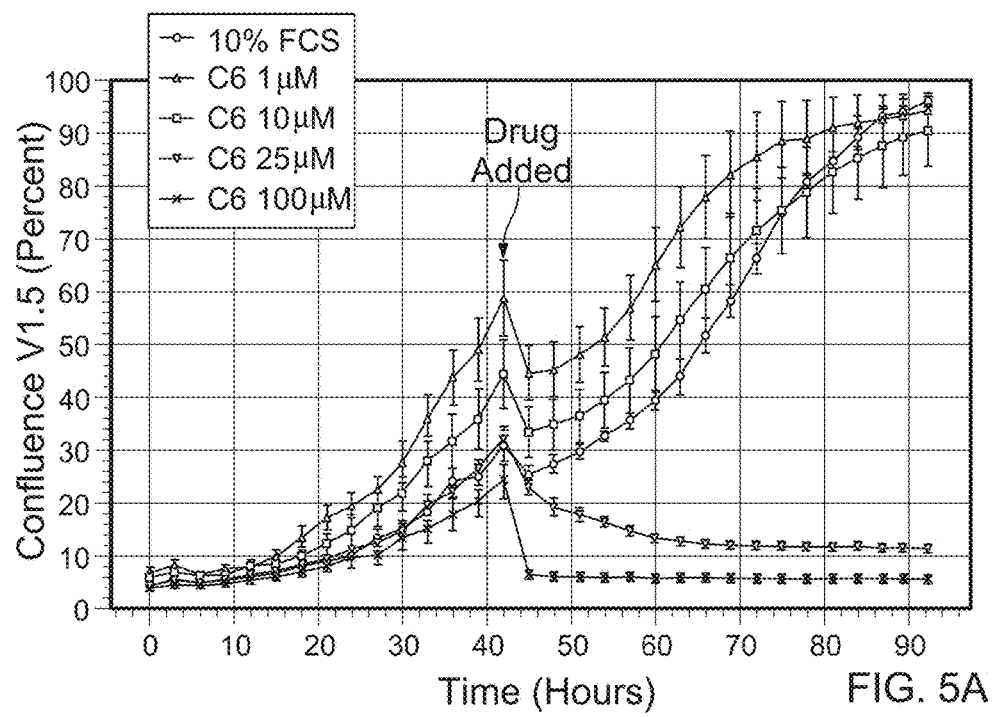
FIG. 5A is a line graph of confluence measurements in dose dependent inhibition by C6 in medulloblastoma (DAOY) cell line.
Figure 5B:
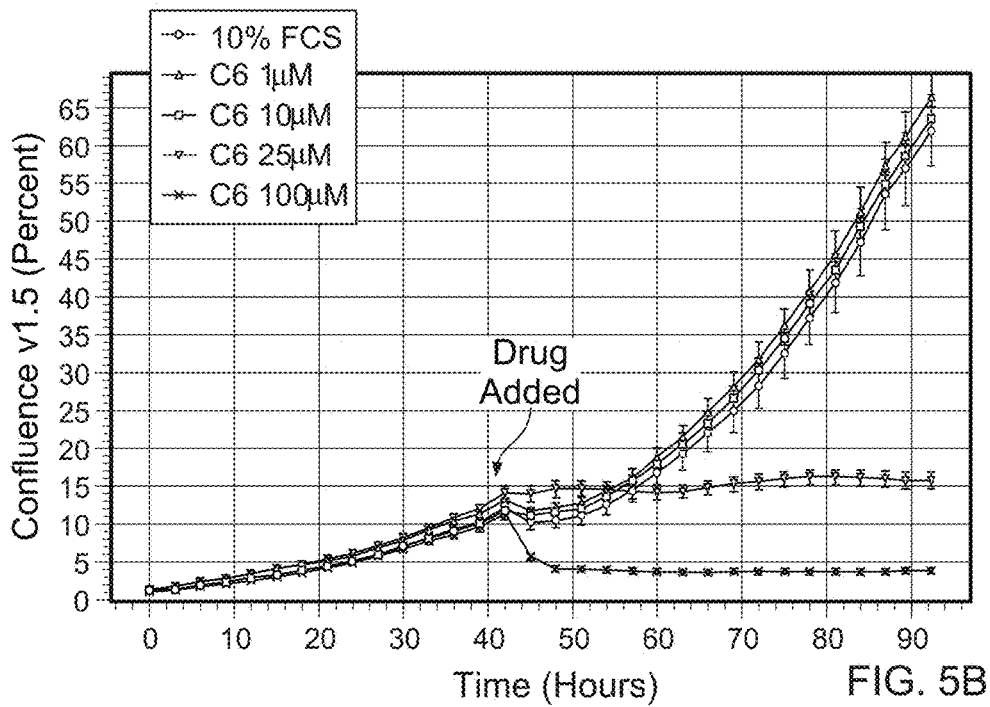
FIG. 5B is a line graph of confluence measurements in dose dependent inhibition by C6 in human colorectal carcinoma cell line.
Figure 6:
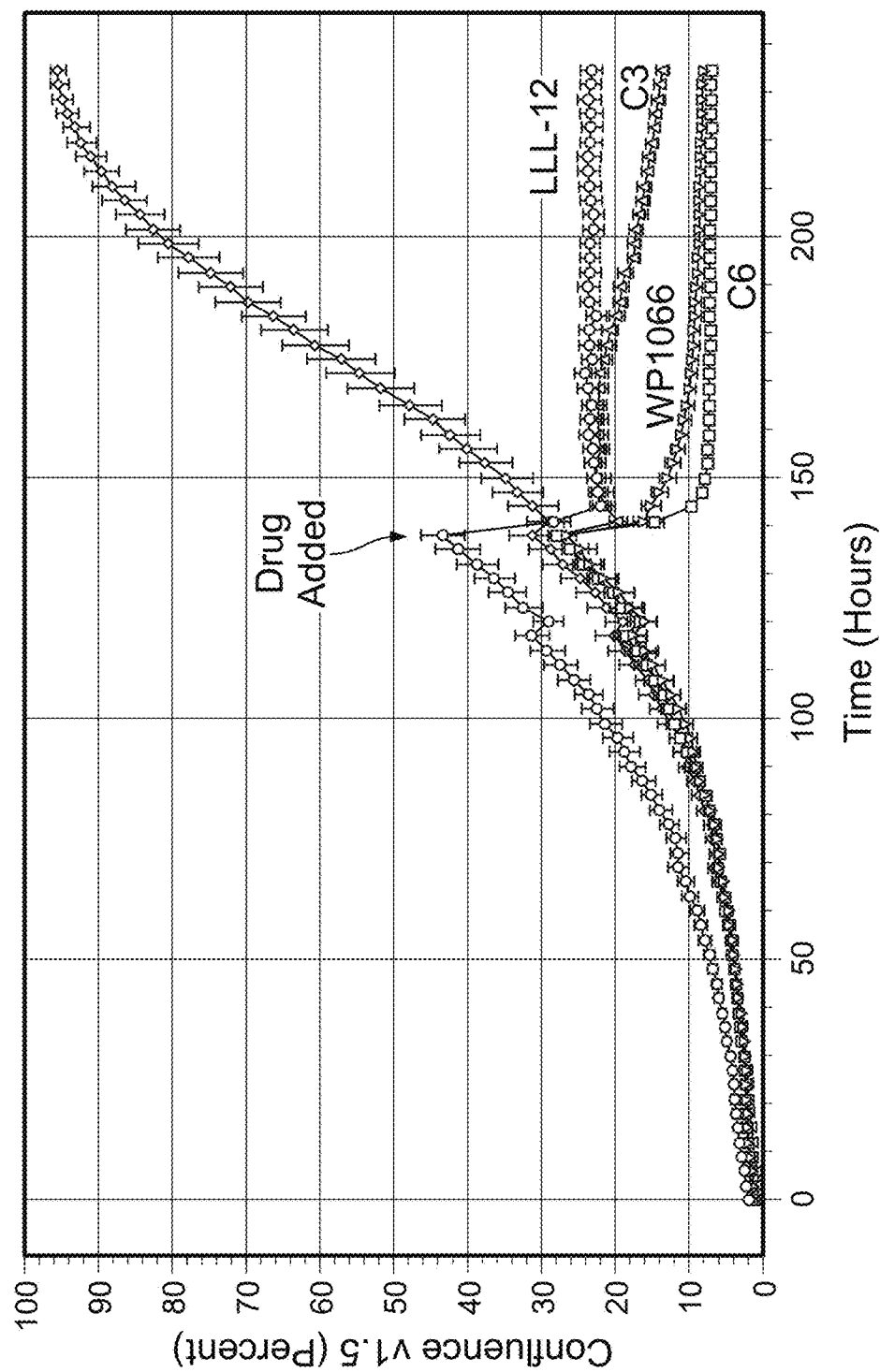
FIG. 6 is a line graph of confluence measurements comparing WP1066 and LLL-12 with C3 and C6.

Pyrazole-based inhibitors were tested for efficacy in stopping tumor cell growth by performing cell proliferation assays in glioblastoma (dBT114), medulloblastoma (DAOY) and human colorectal carcinoma (HCT116) cells lines. Tumor cells were plated in 96-well plates and varying concentrations of inhibitors or DMSO were added initially or after several log-growths of tumor cells. Cell proliferation was determined by measuring cell confluency using an automated system. In dBT114 cells a profound effect was found on tumor cell growth kinetics with C3 and C6 at 50 µM concentration (FIG. 4A). A dose-dependent inhibition of tumor cell proliferation was observed with C6, C4 and C3 (FIG. 4B, only showing C6 data). Similar effects were found on tumor cell proliferation in DAOY and HCT116 tumor cell lines (FIG. 5, again only showing C6 data). The effects of C6 and C3 on tumor cell proliferation were compared to other previously characterized inhibitors, specifically, WP1066 (a Jak2 inhibitor) and LLL-12 (a direct STAT3 inhibitor). A similar inhibitory effect was found on the growth kinetics of dBT114 cells at 50 µM with all compounds tested (FIG. 6).

Figure 7:
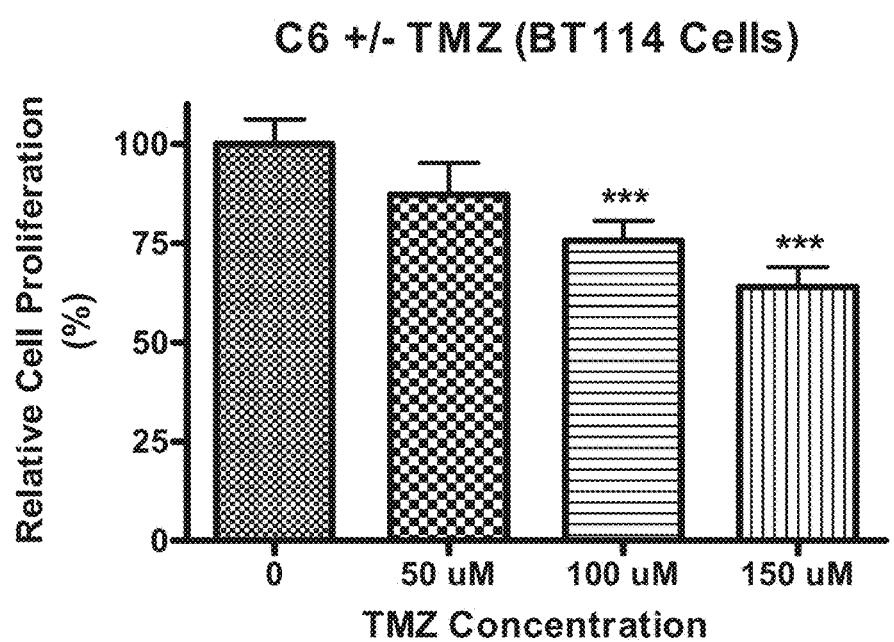
FIG. 7 is a bar graph of dose dependent effect on cell proliferation when C6 is combined with temozolomide (TMZ).

The potential for a synergistic/additive effect between our inhibitors and temozolomide (TMZ) was investigated. Glioblastoma cells (dBT114) were treated with a fixed concentration of C6 (25 µM) and increasing concentrations of TMZ. The combinatorial effects of C6 with TMZ led to a dose-dependent decrease in cellular proliferation (FIG. 7).

Figure 8A:
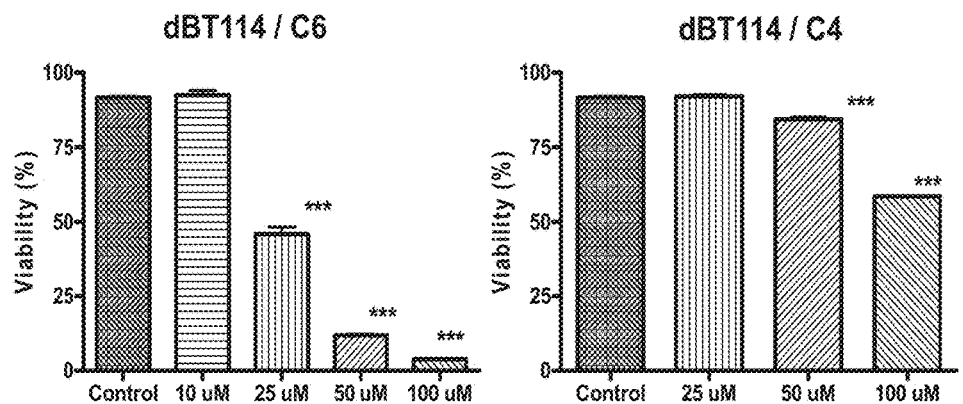
FIG. 8A is a bar graph of dose dependent tumor cell viability in dBT114 cell line.
Figure 8B:
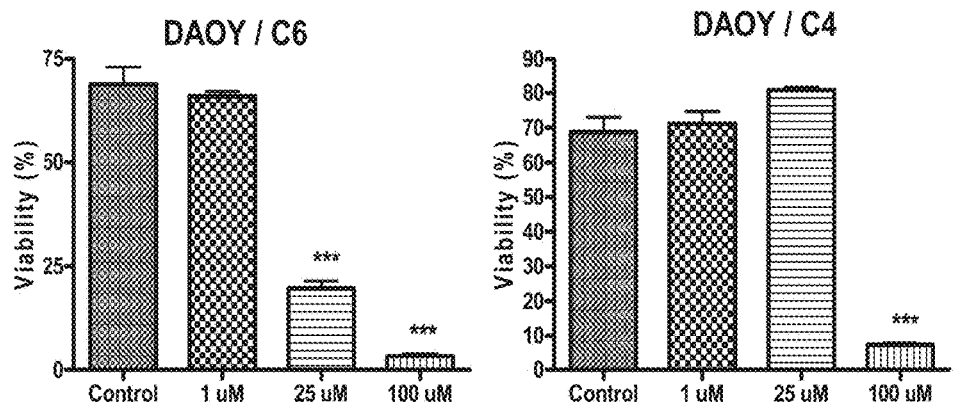
FIG. 8B is a bar graph of dose dependent tumor cell viability in DAOY cell line.
Figure 8C:
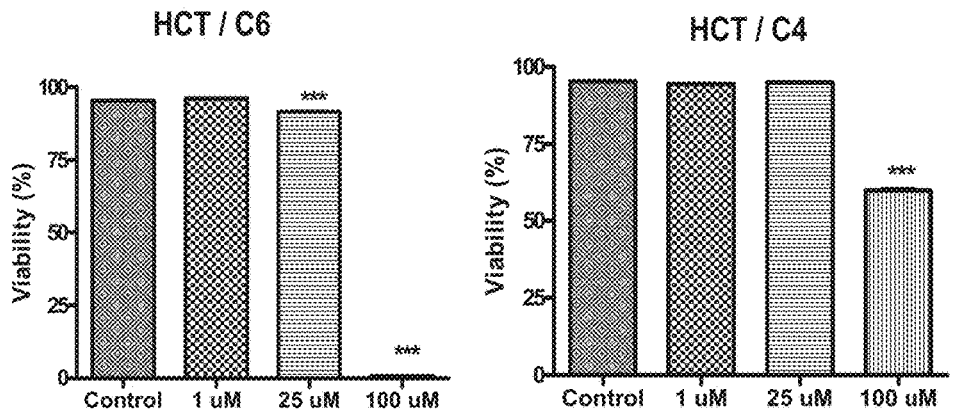
FIG. 8C is a bar graph of dose dependent tumor cell viability in HCT116 cell line.

The compounds were tested for their effect on tumor cell viability by initiating apoptosis through Annexin V-FITC cell staining analysis. Flow cytometric analysis of Annexin V/Propidium Iodine (PI) staining confirmed cell death through apoptosis for C6 and C4 in BT114, DAOY and HCT cell lines in a dose dependent manner. Cell death was most pronounced in DAOY cells, followed by BT114 and then HCT cells (FIG. 8). Additionally, C6 was more potent than C4 in all cell lines tested. The difference in cell death between cell lines may reflect differences in STAT3 signaling between tumor cell types.

Figure 9:
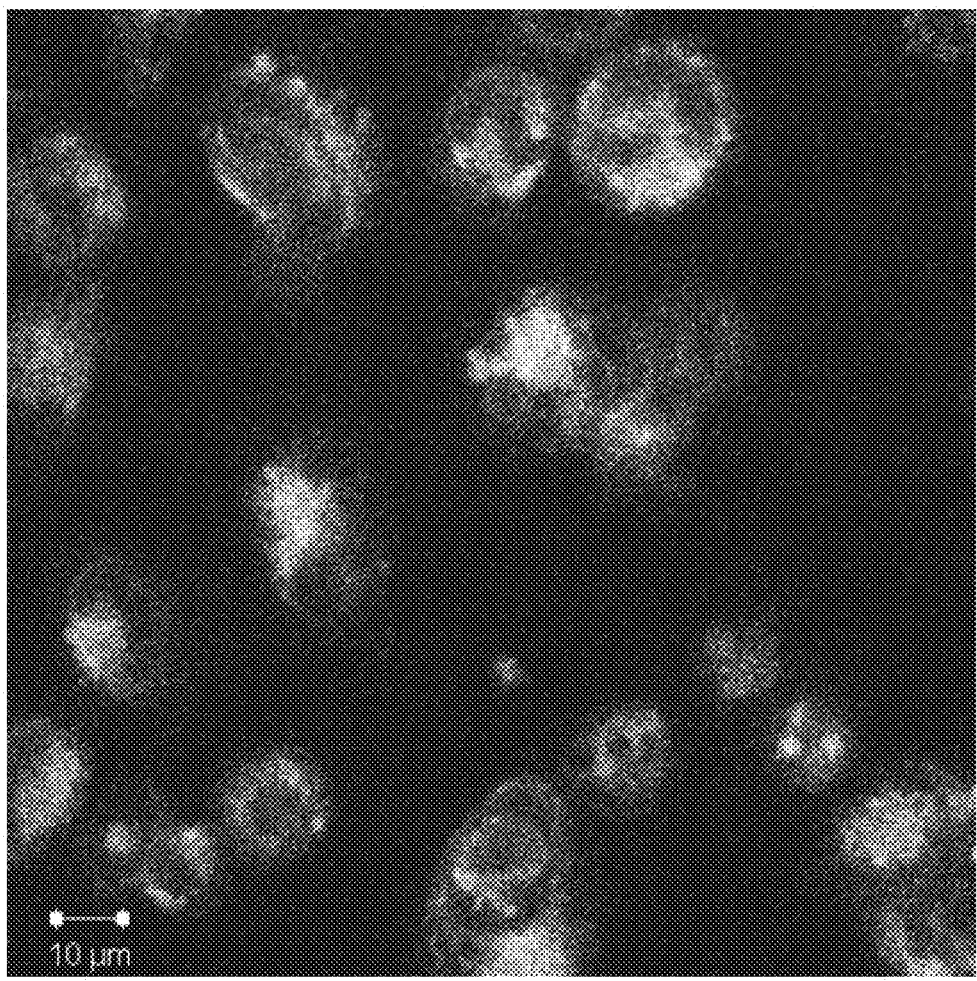
FIG. 9 is a confocal microscopy image of fluorescence due to C9 uptake in living DAOY cells.

Further, live DAOY cells were treated with 50 µM C9 for 30 minutes and then evaluated its uptake with confocal microscopy. FIG. 9 shows strong uptake and fluorescence in living cells.

F. Methods of Use

Methods used to test the effectiveness and specificity of STAT3 inhibitors have been described.

In another aspect, the invention provides a method of modulating an activity of STAT3 which includes, contacting STAT3 with a compound of Formulae I-II, or a pharmaceutically acceptable salt thereof.

Contacting can be in vivo or in vitro. Modulation of an activity can include inhibition or enhancement as compared to the activity in the absence of the compound. Modulation of an activity can also include an increase or decrease in amount of STAT3 as compared to the amount in the absence of the compound. For example, a compound provided herein can modulate the amounts of STAT3, e.g., by inhibiting the phosphorylation of STAT3 monomers, thereby decreasing the amount of phosphorylated STAT3 monomers relative to the amount in the absence of the compound. The modulation of STAT3 can be due to the interaction, e.g., non-covalent binding, of the compound of Formulae I-II, or a pharmaceutically acceptable salt thereof, with STAT3. Non-covalent binding can occur with the SH2 domain. A compound provided herein can modulate an activity of STAT3, e.g., by inhibiting the phosphorylation of STAT3 monomers or by inhibiting the dimerization of phosphorylated STAT3 monomers thereby inhibiting the translocation of STAT3 dimers to the nucleaus and hence the binding of STAT3 dimers to nucleic acid (such as to the specific DNA-response elements in the promoters of target genes). A compound provided herein can modulate the activity of STAT3, e.g., by inhibiting the dimerization of phosphorylated STAT3 monomers, thereby decreasing the amount of phosphorylated STAT3 dimers.

In some embodiments, a compound of Formulae I-II, or a pharmaceutically acceptable salt thereof, modulates the phosphorylation of a monomeric form of STAT3. In some embodiments, a compound of Formulae I-II, or a pharmaceutically acceptable salt thereof, modulates the dimerization of phosphorylated STAT3. In some embodiments, a compound of Formulae I-II, or a pharmaceutically acceptable salt thereof, modulates the amounts of monomeric form of phosphorylated STAT3. In some embodiments, a compound of Formulae I-II or a pharmaceutically acceptable salt thereof modulates the amounts of dimeric form of phosphorylated STAT3. In some embodiments, a compound of Formulae I-II, or a pharmaceutically acceptable salt thereof, modulates the translocation of STAT3 dimer to nucleus. In some embodiments, a compound of Formulae I-II, or a pharmaceutically acceptable salt thereof, modulates the binding of STAT3 dimer to DNA. In some embodiments, a compound of Formulae I-II, or a pharmaceutically acceptable salt thereof, modulates the STAT3 dependent transcriptional activity (such as of proliferation proteins or anti-apoptopic proteins). In some embodiments, a compound of Formulae I-II or a pharmaceutically acceptable salt thereof, modulates a constitutively activated STAT3, e.g., prevents its binding to nucleic acid.

In some embodiments, a compound of Formulae I-II, or a pharmaceutically acceptable salt thereof, is a selective inhibitor of STAT3.

Also described are methods for treating, preventing, or ameliorating one or more symptoms, disorders, or conditions associated with STAT3 activity in a mammal (e.g., a human). The methods can employ a composition comprising any of the compounds provided herein.

In another aspect, the invention provides a method for treating, preventing, or ameliorating one or more symptoms associated with cancer (such as, breast cancer, lung cancer, or brain cancer) including, administering to a subject in need thereof a therapeutically effective amount of a compound of Formula I, or a pharmaceutically acceptable salt thereof.

In some embodiments, the cancer is a solid tumor.

In some embodiments, the cancer is hematological.

In some embodiments, the cancer is lymphoma, leukemia, multiple myeloma, glioblastoma, medulloblastoma, or human colorectal carcinoma.

One or more additional pharmaceutical agents or methods of treatment such as, anti-cancer agents, cytotoxic agents, or anti-cancer therapies (e.g., radiation, hormone, etc.), can be used in combination with the compounds of the present invention for treatment of the diseases, conditions described herein. The agents or therapies can be administered together (e.g., combined into a single dosage form) or sequentially with the compounds of the invention.

In some embodiments, the anti-cancer agents include anti-cancer vaccines, such as, dendritic cells, synthetic peptides, DNA vaccines and recombinant viruses.

In some embodiments, the compounds described herein are used in combination with an alkylating agent.

In some embodiments, the alkylating agent is temozolomide.

In another aspect, the invention provides a method of imaging, the method including obtaining a sample comprising STAT3; contacting the sample with a compound described herein; and detecting emission therefrom to image the sample.

In some embodiments, the sample comprises a cell lysate.

In some embodiments, the compound contacting a sample has a Formula IB.

In some embodiments, a plurality of samples is provided and emission is detected from each of the samples.

In some embodiments, the plurality of samples is in a multi-well plate.

The invention is further described in the following examples, which do not limit the scope of the invention described in the claims.

The insertion and expansion of stents in blood vessels, urinary tracts or other places for preventing restenosis, providing vessel or lumen wall support or reinforcement and for other therapeutic or restorative functions is known. The self-expanding tubular type stent devices for transluminal implantation are generally known. One such device includes a flexible tubular body composed of several individual flexible thread elements each of which extends in a helix configuration with the centerline of the body serving as a common axis. The stents which carry a compound of the invention could be metallic stents, polymeric stents, polyfilamentous, tubular, and/or self-expanding. The general idea of utilizing implanted stents to carry medicinal agents is known. For example, Pinchuk in U.S. Pat. No. 5,092,877, discloses a stent of a polymeric material which may be employed with a coating associated with the delivery of drugs. The compounds of the invention can be applied as a coating on the stent body or impregnated into the polymeric material that constitutes the stent. The stents of the invention can include other therapeutic agents, such as, an anti-restenosis agent.

STAT3 has been shown to be phosphorylated and up-regulated in neointimal lesions in mice upon wire-induced injury. STAT3 phosphorylation could promote proliferation and migration of vascular smooth muscle cells. Localized application of STAT3 inhibitors could thus provide an effective method for prevention and treatment of vascular proliferative diseases. Thus, another aspect of the invention includes a method of treatment for preventing endothelial proliferation by localized administration of a compound of the invention. In some embodiments, the endothelial proliferation is due to vascular injury. In some embodiments, the endothelial proliferation is due to a vascular surgery, transcatheter vascular therapy, vascular grafting, placement of a vascular shunt or placement of an intravascular stent. In some embodiments, the endothelial proliferation is due to a tumor. In some embodiments, the stent comprises the compound of the invention, or a pharmaceutical salt thereof.

EXAMPLES

General:

All chemical solvents and reagents were purchased commercially and used without purification. All reactions were carried out under dry nitrogen and stirred magnetically spectra were obtained on Bruker DRX-500 and Bruker DRX-600 MHz NMR instruments and are referenced to the deuterated solvent peak and are reported in ppm from tetramethylsilane. Chemical shifts are reported in ppm using a solvent resonance as an internal standard. Data are reported as follows: Chemical shift, integration, multiplicity (s=singlet, d=doublet, t=triplet, m=multiplet, bs=broad singlet, bt=broad triplet, dd=doublet of a doublet) and coupling constants. LC-ESI-MS analysis and HPLC purity were performed on a Waters (Milford, Mass.) LC-MS system; a Waters XTerra C18 5 μm column was used; gradients of acetonitrile (ACN) and water with 0.1% formic acid was used as the solvent (5 mL/minute, gradient from 5% ACN to 100% ACN over 1.5 minutes, then plateau at 100% ACN 1.5 minutes-2.0 minutes). Column chromatography was performed with silica gel (E. Merck 60, 230-400 mesh). Thin-layer chromatography (TLC) was performed on silica gel plates.

Example 1

Step 1:

Methyl 2-(4-((tert-butoxycarbonyl)amino)phenyl)acetate (2). To a solution of sodium bicarbonate (4.80 g, 57.25 mmol, 1.0 eq) and methyl 2-(4-aminophenyl)acetate (1) (9.46 g, 57.25 mmol, 1.0 eq) in THF (70 mL) at reflux, a solution of di-tert-butyldicarbonate (15.0 g, 68.7 mmol, 1.2 eq) in THF was added dropwise. The temperature was reduced to 50° C. and the reaction was stirred overnight under a $N_2$ atmosphere. A slight precipitate had formed and was filtered. The solvent was removed in vacuo and the crude product was purified by recrystallization with hexane: ethyl acetate (5:1) to afford 2 (70% yield). $^1$H NMR (DMSO-$d_6$) δ 9.31 (s, 1H), 7.39 (d, J=8.4 Hz, 2H), 7.14 (d, J=8.4 Hz, 2H), 3.61 (s, 2H), 3.59 (s, 3H), 1.48 (s, 9H).

Step 2:

Tert-butyl (4-(4-(4-bromophenyl)-2,4-dioxobutyl)phenyl)carbamate (4). Potassium t-butoxide (4.90 g, 43.87 mmol, 1.1 eq) was dissolved in THF (50 mL) and cooled over ice. 4-Bromoacetophenone (3) (7.92 g, 39.8 mmol, 1.0 eq) in THF was added dropwise to the base over 30 minutes. The solution was brought to room temperature and the protected amine (2) was added in one portion. The reaction was stirred at room temperature for 24 hours. The solvent was removed in vacuo and the product was purified by recrystallization in ethanol (62% yield). $^1$H NMR (DMSO-$d_6$) δ 9.31 (s, 1H), 7.86 (d, J=7.8 Hz, 2H), 7.75 (d, J=6.0 Hz, 2H), 7.42 (d, J=7.2, 2H), 7.21 (d, J=7.8 HZ, 2H), 4.12 (s, 2H), 3.71 (s, 2H), 1.47 (s, 9H).

Step 3:

Tert-butyl (4-((5-(4-bromophenyl)-1-(4-sulfamoylphenyl)-1H-pyrazol-3-yl)methyl)phenyl)carbamate (6). Dione 4 (3.45 g, 8.1 mmol, 1.0 eq) and 4-hydrazinylbenzenesulfonamide HCl salt (2.00 g, 8.9 mmol, 1.1 eq) were dissolved in ethanol and brought to reflux. This was reacted overnight and TLC analysis showed the starting materials had been consumed. A fine precipitate had formed and was removed by vacuum filtration. The solvent was removed in vacuo to afford the boc protected compound 6 and was deprotected without further purification.

Step 4:

3-(4-Aminobenzyl)-5-(4-bromophenyl)-1-(4-aminosulfonylphenyl)-1H-pyrazole (C1). Trifluoroacetic (15 mL) was added neat to the boc-protected pyrazole 6 (8 mmol). After 5 minutes, TLC analysis showed all the starting material had been consumed. The crude product was added to water (10 mL) and neutralized with sodium bicarbonate. The solvents were removed in vacuo and the residue was purified by recrystallization in ethanol to give C1 (41% yield over 2 steps). $^1$H NMR (DMSO-$d_6$) δ 7.83 (d, J=7.8 Hz, 2H), 7.60, (d, J=9.0 Hz, 2H), 7.47-7.42 (m, 4H), 7.34 (d, J=8.4 Hz, 2H), 7.19 (d, J=8.4 Hz, 2H), 7.07 (d, J=7.8 Hz, 2H), 6.54 (s, 1H), 3.98 (s, 2H); LRMS (ES+) calculated for $[C_{22}H_{19}BrN_4O_2S+H]$ 483.05 found 483.08; HPLC $t_R$=0.86 min (96.2% purity).

Example 2

Step 1:

Methylaminocarbonylmethoxy-acetic acid (9). To diglycolic anhydride (5.0 g, 43.08 mmol, 1.0 eq) a 2M THF solution of methyl amine (25 mL, ~43 mmol) was added in two portions. After 18 hours the reaction mixture was concentrated in vacuo to afford the crude product as an oil. After further removal of solvent under high vacuum (24 h) the product crystallized to give 6.34 g (quantitative) of 9; mp 57° C.; $^1$H NMR (DMSO-$d_6$) 12.76 (b s, 1H), 7.78 (br s, 1H), 4.08 (s, 2H), 3.93 (s, 2H), 2.61 (d, J=4.8 Hz, 3H).

Step 2:

3-[{2-[(Methylaminocarbonyl)-methoxy]-acetyl}-(4-aminobenzyl)]-5-(4-bromophenyl)-1-(4-aminosulfonylphenyl)-1H-pyrazole (C3). A solution containing carboxylic acid 9 (0.027 g, 0.18 mmol, 1.0 eq), HBTU (0.069 g, 0.18 mmol, 1.1 eq), DIPEA (0.047 g, 0.36 mmol, 2.2 eq) in DMF (2 mL) was stirred for 30 min. C1 (0.080 g, 0.17 mmol, 1.0 eq) in DMF (1 mL) was added to the mixture and allowed to react at room temperature overnight. The product was precipitated/oiled out by addition to diethyl ether and hexane. The oil was washed successively with portions of diethyl ether (50 mL), and hexanes (50 mL). Purification by flash chromatography (silica gel, D/M/A 94.5/5/0.5, v/v/v) gave C3 (64.3% yield). $^1$H NMR (DMSO-$d_6$) 9.96 (b s, 1H), 8.09 (b s, 1H), 7.83 (d, J=8.4 Hz, 2H), 7.60-7.58 (m, 4H), 7.46-7.43 (m, 4H), 7.32 (d, J=8.4 Hz, 2H), 7.20 (d, J=8.4 Hz), 6.54 (s, 1H), 4.10 (s, 2H), 4.04 (s, 2H), 3.98 (s, 2H), 2.67 (d, J=4.8 Hz); LRMS (ES+) calculated for [$C_{27}H_{26}BrN_5O_5S$+H] 612.09 found 612.15; HPLC $t_R$=0.97 min (99.3% purity).

Example 3

3-(4-Acetamidebenzyl)-5-(4-bromophenyl)-1-(4-aminosulfonylphenyl)-1H-pyrazole (C4). Amine C1 (0.067 g, 0.15 mmol, 1.0 eq) was dissolved in glacial acetic acid (3 mL) and acetyl chloride was added dropwise (0.123, 1.56 mmol, 10.0 eq). A precipitate formed immediately. The precipitate was collected after 30 minutes, washed with a solution of sodium bicarbonate in water and extracted with ethyl acetate. The solvent was removed in vacuo and the product was washed with ether to afford C4 (quantitative). $^1$H NMR (DMSO-$d_6$) δ 9.89 (b s, 1H), 7.83 (d, J=9.0 Hz, 2H), 7.59 (d, J=8.4 Hz, 2H), 7.52 (d, J=8.4 Hz, 2H), 7.46-4.432 (m, 4H), 7.27 (d, J=8.4 Hz, 2H), 7.19 (d, J=8.4 Hz, 2H), 6.53 (s, 1H), 3.95 (s, 2H), 2.03 (s, 3H); LRMS (ES+) calculated for [$C_{24}H_{21}BrN_4O_3S$+H] 525.06 found 525.13; HPLC $t_R$=1.03 min (>99.0% purity).

Example 4

3-(4-Benzamide-benzyl)-5-(4-bromophenyl)-1-(4-aminosulfonylphenyl)-1H-pyrazole (C5). Amine C1 (0.050 g, 0.10 mmol, 1.0 eq) was placed in a glass vial and benzoyl chloride (0.043 g, 0.30 mmol, 3.0 eq) was added dropwise and mixed into a paste. This was allowed to react for 15 minutes, then a solution of sodium bicarbonate was added (3 mL). The product was extracted with ethyl acetate and the solvent was removed in vacuo to afford C5 (85.3%). $^1$H NMR (DMSO-$d_6$) δ 10.24 (b s, 1H), 7.95 (d, J=9.0 Hz, 2H), 7.83 (d, J=9.0 Hz, 2H), 7.73 (d, J=8.3 Hz, 2H), 7.61-7.58 (m, 3H), 7.54 (t, J=7.8 Hz, 2H), 7.45 (d, J=8.4 Hz, 2H), 7.39-7.34 (m, 4H), 7.21 (d, J=8.4 Hz, 2H), 6.55 (s, 1H), 4.00 (s, 2H); LRMS (ES+) calculated for [$C_{29}H_{23}BrN_4O_3S$+H] 587.08 found 587.18; HPLC $t_R$=1.24 min.

Example 5

Step 1:

1-(4-Bromophenyl)-6-methylheptane-1,3-dione (10). Potassium t-butoxide (6.20 g, 55.22 mmol, 1.1 eq) was dissolved in THF (35 mL) and cooled over ice. 4-Bromoacetophenone (10.00 g, 50.2 mmol, 1.0 eq) in THF was added dropwise to the base over 30 minutes. The solution was brought to room temperature and methyl-4-methylpentanoate was added in one portion. The reaction was stirred at room temperature overnight. The solvent was removed in vacuo and suspended in water. The base was neutralized with 1N HCl and the crude product was extracted into hexane. After removal of the solvent, the crude product was further purified by flash chromatography (silica gel, hexane/ethyl acetate 96/4, v/v) to afford 10 (34.7% yield). $^1$H NMR (DMSO-$d_6$) [Enol form] δ 7.87 (d, J=9.0 Hz, 2H), 7.76 (d, J=9.0 Hz, 2H), 6.16 (s, 1H), 2.47 (t, J=7.8 Hz, 2H), 1.60-1.56 (m, 1H), 1.54-1.50 (m, 2H), 0.91 (d, J=6.6 Hz, 6H).

Step 2:

5-(4-Bromophenyl)-3-(isopentyl)-1-(4-aminosulfonylphenyl)-1H-pyrazole (C6), 3-(4-Bromophenyl)-5-(isopentyl)-1-(4-aminosulfonylphenyl)-1H-pyrazole (C7), 5-(Phenyl)-3-(isopentyl)-1-(4-aminosulfonylphenyl)-1H-pyrazole (C8), and 3-(Phenyl)-5-(isopentyl)-1-(4-aminosulfonylphenyl)-1H-pyrazole (C9). Dione 10 (2.83 g, 9.52 mmol, 1.0 eq) and 4-hydrazinylbenzenesulfonamide HCl salt (2.34 g, 10.47 mmol, 1.1 eq) were dissolved in ethanol and brought to reflux. This was reacted overnight. After removal of the solvent, the crude product was further purified by flash chromatography (silica gel, D/CAN, 95/5, v/v) to afford C6 (47.3% yield) and C7 (26.1%). C6: $^1$H NMR (DMSO-$d_6$) δ 7.83 (d, J=9.0 Hz, 2H), 7.61 (d, J=9.0 Hz, 2H), 7.58-7.41 (m, 4H), 7.22 (d, J=9.0 Hz, 2H), 6.59 (s, 1H), 2.65 (t, J=8.4 Hz, 2H), 1.67-1.62 (m, 1H), 1.60-1.56 (m, 2H), 0.95 (d J=6.6 Hz, 6H); LRMS (ES+) calculated for [$C_{20}H_{22}BrN_3O_2S$+H] 448.07 found 448.13; HPLC $t_R$=1.34 min (95.0% purity). C7: $^1$H NMR (DMSO-$d_6$) δ 7.98 (d, J=8.6 Hz, 2H), 7.84 (d, J=8.5 Hz, 2H), 7.82 (d, J=8.6 Hz, 2H), 7.64 (d, J=8.5 Hz, 2H), 7.52 (s, 2H), 6.93 (s, 1H), 2.78 (t, J=7.9 Hz, 2H), 1.60-1.50 (m, 3H), 0.86 (d, J=6.5 Hz, 6H); LRMS (ES+) calculated for [$C_{20}H_{22}BrN_3O_2S$+H] 448.07 found 448.13. C9: $^1$H NMR (DMSO-$d_6$) δ 7.99 (d, J=8.5, 2H), 7.88 (d, J=7.6, 2H), 7.82 (d, J=8.5, 2H), 7.52 (s, 2H), 7.44 (t, J=7.6, 2H), 7.36 (t, J=7.2, 1H), 6.86 (s, 1H), 2.79 (t, J=8.0, 2H), 1.60-1.51 (m, 3H), 0.87 (d, J=6.4 Hz, 6H). LRMS (ES+) calculated for [$C_{20}H_{23}N_3O_2S$+H] 370.16 found 370.25; HPLC $t_R$=1.31 min (99.0% purity).

Example 6

Step 1:

{[7-(2-Carboxymethoxy-acetylamino)heptylaminocarbonyl]-methoxy}-acetic acid (8). To a stirred solution of diglycolic anhydride (5.00 g, 43.0 mmol, 2.2 eq) in DMF (10 mL), 1-7-diaminoheptane (2.55 g, 19.55 mmol, 1.0 eq) in DMF (4 mL) was added dropwise and the mixture was then stirred at room temperature overnight. The solution was added to ethyl ether (25 mL) and the solvents were removed in vacuo and the product was further dried on a vacuum pump overnight. The product crystallized during the drying process to yield 8 (quantitatively). $^1$H NMR (DMSO-$d_6$) 12.81 (br s, 2H), 7.83 (t, J=6.0 Hz, 2H), 4.11 (s, 4H), 3.95 (s, 4H), 3.09 (q, J=13.8, 7.2 Hz, 4H), 1.42 (q, J=14.4, 7.2 Hz, 4H), 1.28-1.21 (m, 6H).

Step 2:

3-[{2-[(7-{2-[((4-((5-(4-Bromophenyl)-1-(4-sulfamoylphenyl)-1H-pyrazol-3-yl)methyl)phenyl)aminocarbonyl)-methoxy]-acetylamino}-heptylaminocarbonyl)-methoxy]-acetyl}-(4-aminobenzyl)]-5-(4-bromophenyl)-1-(4-aminosulfonylphenyl)-1H-pyrazole (C10). A solution containing biscarboxylic acid 8 (0.05 g, 0.14 mmol, 1.0 eq), HBTU (0.11 g, 0.28 mmol, 2.0 eq), DIPEA (0.07 g, 0.56 mmol, 4.0 eq) in DMF (2 mL) was stirred for 30 min. C1 (0.14 g, 0.29 mmol, 2.1 eq) in DMF (2 mL) was added to the mixture and allowed to react at room temperature for 48 hours. The product was precipitated by addition to diethyl ether and hexane. The solid was washed successively with portions of diethyl ether (50 mL), and hexanes (50 mL). Purification by flash chromatography (silica gel, D/M/A (Dichloromethane/Methanol/Ammonium Hydroxide), 94.5/5/0.5, v/v/v) gave C10 (52.1% yield). $^1$H NMR (DMSO-d$_6$) 10.01 (b s, 2H), 8.11 (b s, 2H), 7.83 (d, J=7.2 Hz, 4H), 7.58 (d, J=8.4 Hz, 8H), 7.46-7.43 (m, 8H), 7.31 (d, J=8.4 Hz, 4H), 7.19 (d, J=7.2 Hz, 4H), 6.52 (s, 2H), 4.14 (s, 4H), 4.03 (s, 4H), 3.97 (s, 4H), 3.14-3.10 (unresolved, 4H), 1.44-1.42 (m, 4H), 1.28-1.24 (m, 6H); LRMS (ES+) calculated for [C$_{59}$H$_{60}$Br$_2$N$_{10}$O$_{10}$S$_2$+H] 1291.24 found 1291.29; HPLC t$_R$=1.18 min (99.1% purity).

Example 7

Western Blot Analysis: Prior to analysis, cells were washed twice in cold phosphate buffered saline (PBS) and flash frozen in 200 μL of lysis buffer (50 mm/L NaCl, 50 mmol/L NaF, 50 mmol/L sodium pyrophosphate, 5 mmol/L EDTA, 5 mmol/L EGTA, 2 mmol/L Na$_3$VO$_4$, 1% Triton X-100, 0.5 mmol/L PMSF, 10 mg/ml leupeptin, 10 mmol/L HEPES, pH 7.4) in a ethanol/dry ice bath followed by scraping and a 5 second sonication to achieve a homogeneous solution. Sample protein concentrations were determined using the Bradford protein assay kit (Bio-Rad, Hercules, Calif.). To characterize changes in protein levels in whole cell lysates, 10 μg of total protein was size fractioned by 12% SDS-PAGE, transferred to nitrocellulose and stained with Ponceau-S stain to ensure equal protein loading. For Western blot analysis, membranes were incubated for 1 hour in blocking solution containing 1% dry milk in PBS-T, followed by an overnight incubation with either anti-Stat3 (Santa Cruz Biotechnology, Santa Cruz, Calif.,) or anti-Phospho-Stat3 (Santa Cruz). Nitrocellulose membranes were then incubated for 1 hour with horseradish peroxidase conjugated anti-IgG antibodies and visualized using Super Signal West Pico enhanced chemiluminescence detection (Thermo Scientific, Waltham, Mass.).

Example 8

IncuCyte Cell Proliferation Assay: Cell proliferation assays were performed on dBT114, DAOY and HCT116 cells using an IncuCyte 2011A microplate imager (Essen BioScience, Ann Arbor, Mich.). Cells were plated at a density of 3000 cells per well in a 96 well plate and allowed to reach exponential growth phase prior to the addition of test compounds. Cell confluence was measured optically every three hours for up to 90 hours.

Example 9

Figure 10A:
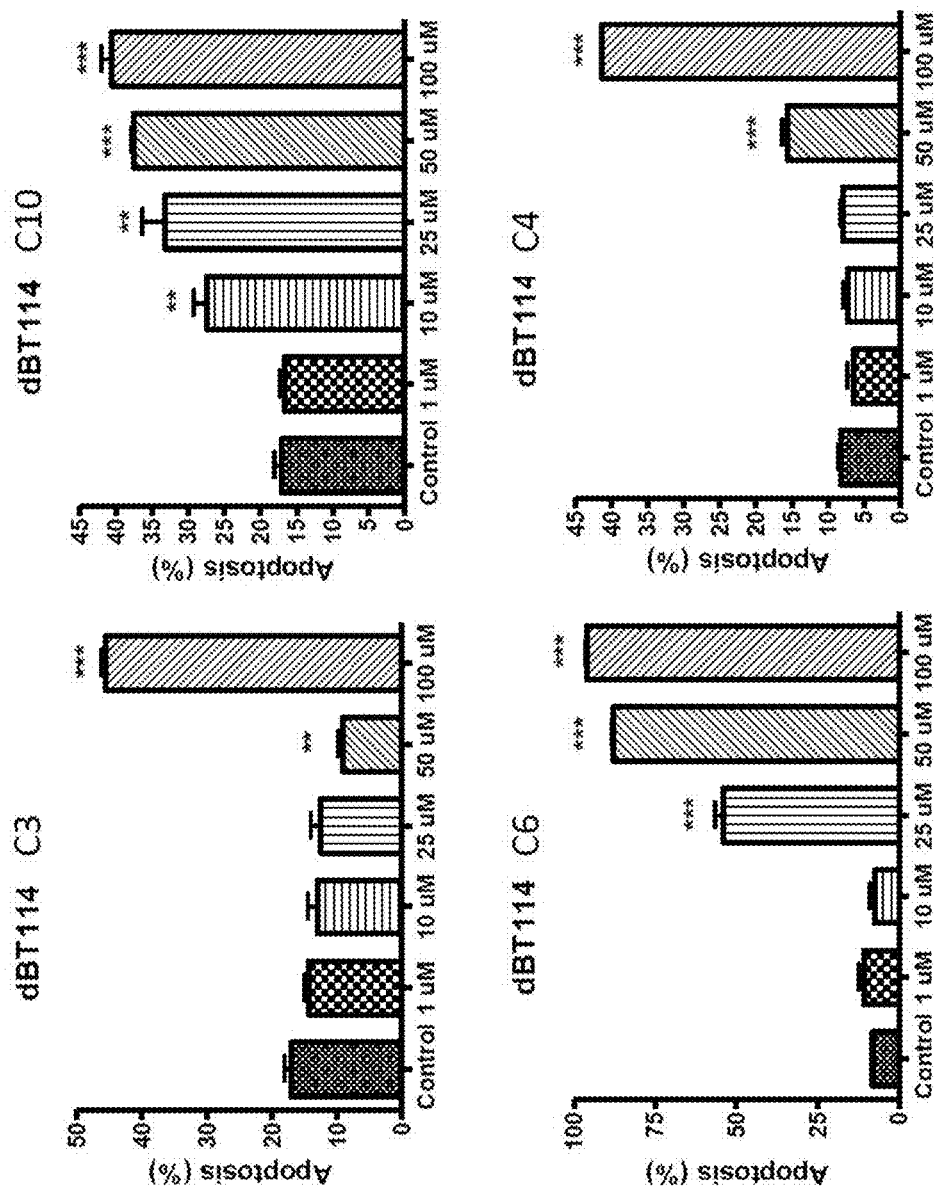
FIG. 10A is a bar graph of dose-dependent apoptosis in human glioma dBT114 cells induced by C3, C10, C6, and C4.
Figure 10B:
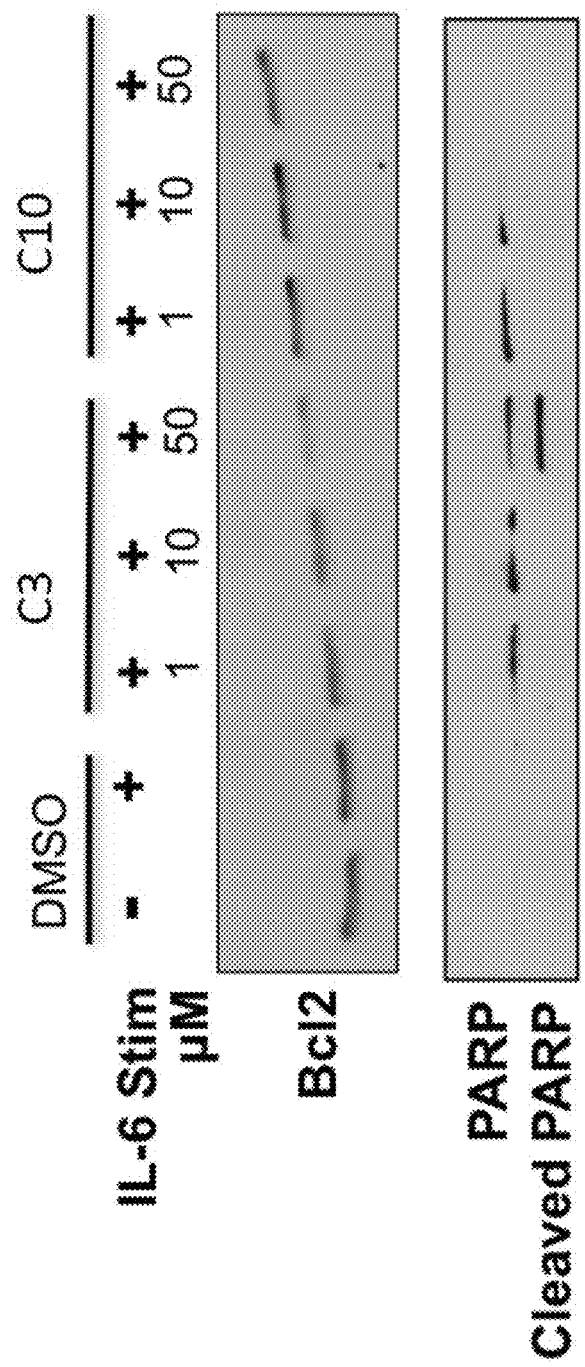
FIG. 10B is an image of dose-dependent reduction in Bcl2 and increase in cleaved PARP in response to C3 and C10.

Apoptosis Assay: Analysis of cell death through an apoptosis pathway was determined using an Annexin V apoptosis detection kit (Calbiochem, Rockland, Mass.). dBT114, DAOY and HCT116 cells were plated in 6-well tissue culture plates at a density of 500 cells per well and allowed to reach 60% confluence prior to addition of test compounds for 24 hours. Floating and adherent cells were harvested and stained with FITC-labeled Annexin V and propidium iodide for 15 minutes at room temperature in the dark. The cells were then washed with cold binding buffer and immediately analyzed by flow cytometry for cells staining positive for both Annexin V and propidium iodide. FIG. 10A shows dose-dependent apoptosis in human glioma dBT114 cells induced by STAT3 inhibitors C3, C10, C6, and C4, detected by Annevin V flow cytometry (results=mean+/−standard deviation, n=3). FIG. 10B shows dose-dependent reduction in Bcl2 and increase in cleaved PARP suggesting apoptosis in response to STAT3 inhibitors C3 and C10.

Example 10

Plasma Stability Study: Samples were analyzed using LC-ESI-MS. The samples (25 uM) were incubated in human plasma at 37 degrees Celsius for 96 hours. Aliquots (100 uL) were taken at time points 0 h, 3 h, 6 h, 12 h, 24 h, 48 h, and 96 h and frozen for later analysis. Analysis began by allowing the samples to warm-up to room temperature. Ethyl acetate (800 uL) and sodium acetate (100 uL, 0.1M solution) were added to the samples, which were then mixed for 15 minutes. Five hundred L of ethyl acetate was removed and dried down over nitrogen gas and reconstituted in 100 μL of 1:1 DMSO:Ethyl Acetate and 400 μL of water. This solution was then injected directly into the LC-MS unit for analysis. Standard calibration curves for each compound were made using concentrations ranging from 0.1 μM to 100 μM and plasma stability was calculated relative to the concentration at time point 0 h. Plasma stability of compounds C6, C3, and C10 are shown in FIG. 11.

Example 11

Figure 12:
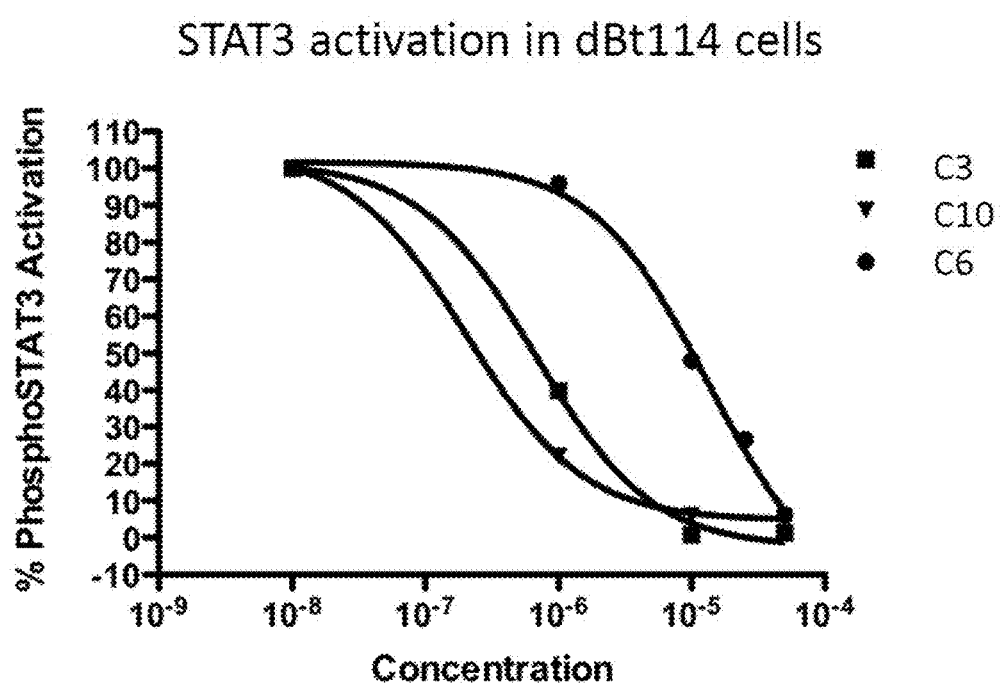
FIG. 12 is a line graph of the half-maximal inhibitory concentrations ($IC_{50}$) for blocking STAT3 activation in dBT114 cells for C3, C10, and C6.

Western Densitometry—Determination of Half-Maximal Inhibitory Concentration for Activating STAT3: Dose Response Curves Half-maximal inhibitory concentrations for activating STAT3 (IC$_{50}$ values) were calculated in BT114 cells from western blot data. The original western blot films were analyzed by densitometric analysis using the software program NIH Image (available at rsb.info.nih.gov/nih-image/). Standard dose-response curves were then created using the software program Prism 5. The half-maximal inhibitory concentrations (IC$_{50}$) for blocking STAT3 activation in dBT114 cells were determined to be 207 nM for compound C10, 670 nM for compound C3, and 13.4 μM for compound C6 (FIG. 12), and greater than 50 μM for compound C4.

Example 12

Figure 13:
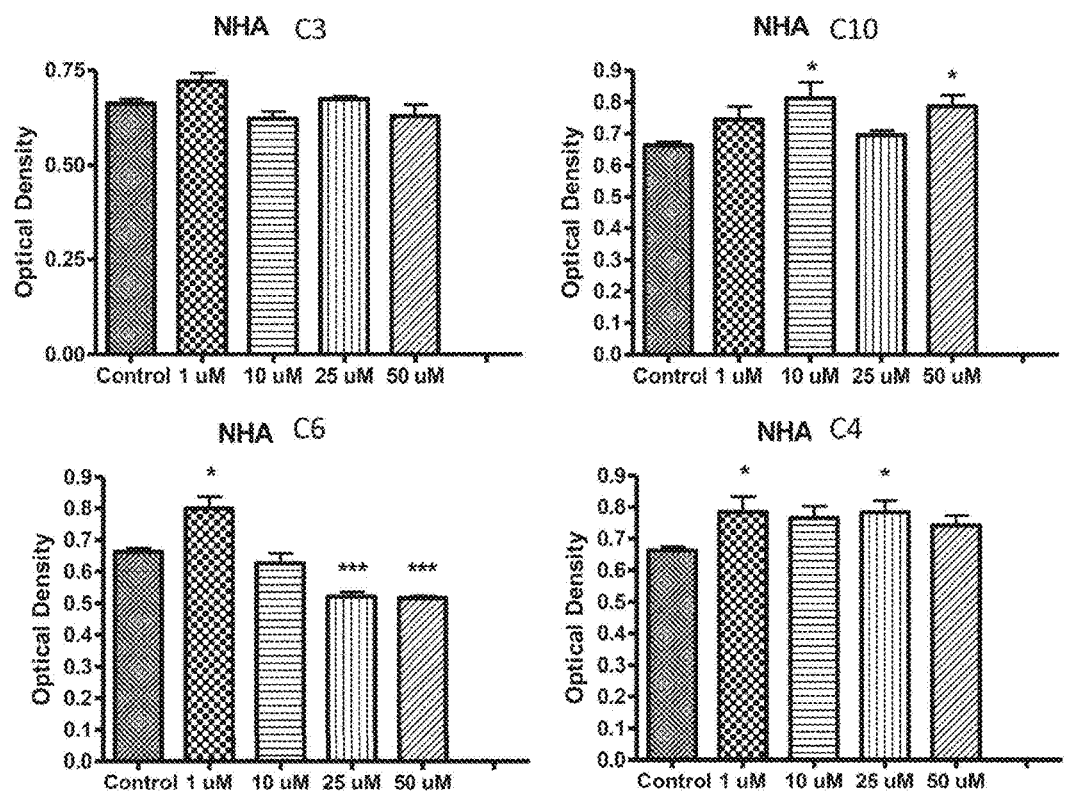
FIG. 13 is a bar graph of metabolic activity of normal human astrocytes (NHA) after 24 hour exposure to increasing concentrations of C3, C10, C6, or C4.

MTT Cell Proliferation Assay: Normal Human Astrocytes (Lonza) and human BT114 cells were plated at a density of 5000 cells per well in a 96-well tissue culture plate and incubated at 37° C. in the presence of 5% CO$_2$ for 24 hours. Cell proliferation was determined using the CellTiter 96 Cell Proliferation Assay (Promega). After 24 hours cells were refed with normal media and MTT dye solution was added according to manufacturer's protocol. After 4 hours the reaction was stopped and absorbance was measured at 570 nm using a 96 well plate reader. FIG. 13 shows metabolic activity (measured by MTS colorimetric assay) of normal human astrocytes (NHA) after 24 hour exposure to increasing concentrations of STAT3 inhibitors C3, C10, C6, or C4. (n=4). Although there is minor variation both up and down, there is no clear pattern of increased or decreased metabolic activity in normal human astrocytes with these STAT3 inhibitors.

A number of embodiments of the invention have been described. Nevertheless, it will be understood that various modifications may be made without departing from the spirit and scope of the invention. Accordingly, other embodiments are within the scope of the following claims. It is to be further appreciated that certain features of the disclosure, which are, for clarity, described in the context of separate embodiments, can also be provided in combination in a single embodiment. Conversely, various features which are, for brevity, described in the context of a single embodiment, can also be provided separately or in any suitable subcombination.

What is claimed is:

1. A compound selected from:

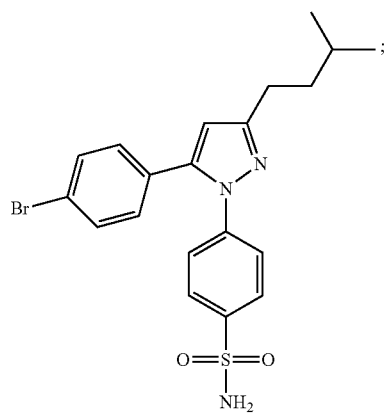
(C6)

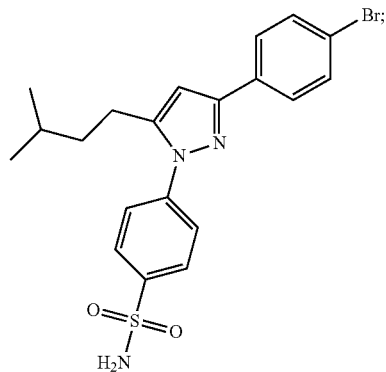
(C7)

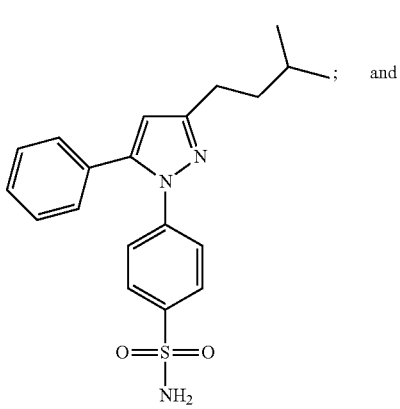
(C8)
and

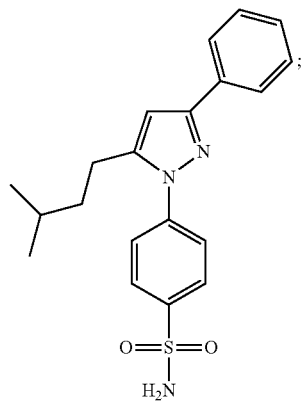
(C9)

or a pharmaceutically acceptable salt thereof.

2. A pharmaceutical composition comprising a compound of claim 1, or a pharmaceutically acceptable salt thereof, and a pharmaceutically acceptable carrier.

3. A method of inhibiting activation of STAT3 or initiating apoptosis in a cancer cell, wherein the cancer is selected from human colorectal carcinoma, lymphoma, leukemia, multiple myeloma, breast cancer, lung cancer, and brain cancer, the method comprising contacting the cell with a compound of claim 1, or a pharmaceutically acceptable salt thereof.

4. The method of claim 3, wherein the brain cancer is selected from glioblastoma and medulloblastoma.

5. A method for treating cancer in a subject, wherein the cancer is selected from human colorectal carcinoma, lymphoma, leukemia, multiple myeloma, breast cancer, lung cancer, and brain cancer, the method comprising administering to the subject in need thereof a therapeutically effective amount of a compound of claim 1, or a pharmaceutically acceptable salt thereof.

6. The method of claim 5, wherein the brain cancer is selected from glioblastoma and medulloblastoma.

7. The method of claim 5, wherein the compound is used in combination with an anti-cancer agent.

8. The method of claim 7, wherein the anti-cancer agent is temozolomide.

9. The compound of claim 1, wherein the compound is:

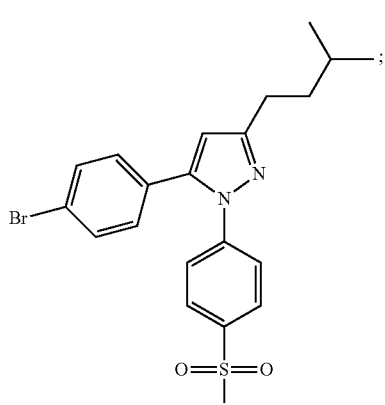
(C6)

or a pharmaceutically acceptable salt thereof.

* * * * *